United States Patent
Kiyokane et al.

(10) Patent No.: US 12,106,466 B2
(45) Date of Patent: Oct. 1, 2024

(54) PHOTOGRAPHING CONDITION DETERMINING METHOD FOR METAL STRUCTURE, PHOTOGRAPHING METHOD FOR METAL STRUCTURE, PHASE CLASSIFICATION METHOD FOR METAL STRUCTURE, PHOTOGRAPHING CONDITION DETERMINING DEVICE FOR METAL STRUCTURE, PHOTOGRAPHING DEVICE FOR METAL STRUCTURE, PHASE CLASSIFICATION DEVICE FOR METAL STRUCTURE, MATERIAL PROPERTY ESTIMATING METHOD FOR METAL MATERIAL, AND MATERIAL PROPERTY ESTIMATING DEVICE FOR METAL MATERIAL

(71) Applicant: JFE Steel Corporation, Tokyo (JP)

(72) Inventors: Naoya Kiyokane, Tokyo (JP); Yoshie Obata, Tokyo (JP); Shin Ishikawa, Tokyo (JP); Takako Yamashita, Tokyo (JP); Takeshi Nishiyama, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 21 days.

(21) Appl. No.: 17/915,126

(22) PCT Filed: Mar. 8, 2021

(86) PCT No.: PCT/JP2021/009006
§ 371 (c)(1),
(2) Date: Sep. 28, 2022

(87) PCT Pub. No.: WO2021/199937
PCT Pub. Date: Oct. 7, 2021

(65) Prior Publication Data
US 2023/0153976 A1    May 18, 2023

(30) Foreign Application Priority Data
Mar. 31, 2020   (JP) .................... 2020-063414

(51) Int. Cl.
*G01N 1/32*      (2006.01)
*G01N 33/204*    (2019.01)
(Continued)

(52) U.S. Cl.
CPC ............ *G06T 7/0004* (2013.01); *G01N 1/32* (2013.01); *G01N 33/204* (2019.01); *G06V 10/10* (2022.01);
(Continued)

(58) Field of Classification Search
CPC ...... G06T 7/0004; G01N 33/204; G01N 1/32; G06V 20/70; G06V 10/10; G06V 10/993; G06V 10/764; H04N 23/64
(Continued)

(56) References Cited

U.S. PATENT DOCUMENTS

| 4,548,903 A | 10/1985 | Weiss et al. |
| 2020/0410270 A1 | 12/2020 | Naruse et al. |

FOREIGN PATENT DOCUMENTS

| EP | 4 099 012 A1 | 12/2022 |
| JP | S62-79361 A | 4/1987 |

(Continued)

OTHER PUBLICATIONS

Partial Supplementary European Search Report dated Jul. 14, 2023, of counterpart European U.S. Appl. No. 21/782,081.
(Continued)

*Primary Examiner* — Nguyen T Truong
(74) *Attorney, Agent, or Firm* — DLA Piper LLP (US)

(57) ABSTRACT

A photographing condition determining method includes: photographing a part of a metal structure of a metal material
(Continued)

subjected to predetermined sample preparation under a predetermined photographing condition; assigning, to pixels corresponding to one or a plurality of predetermined phases of the metal structure, labels of respective phases for a photographed image; calculating one or more feature values for a pixel to which a label of one of the assigned phases; classifying the phases of the metal structure of the image by inputting a calculated feature value to a model, which has been learned in advance using feature values assigned with labels of respective phases as input and labels of the respective phases as output, and acquiring a label of a phase of a pixel corresponding to the input feature value; and determining a photographing condition when other parts of the metal structure are photographed based on a classification result.

20 Claims, 18 Drawing Sheets

(51) Int. Cl.
*G06T 7/00* (2017.01)
*G06V 10/10* (2022.01)
*G06V 10/764* (2022.01)
*G06V 10/98* (2022.01)
*G06V 20/70* (2022.01)
*H04N 23/60* (2023.01)

(52) U.S. Cl.
CPC .......... *G06V 10/764* (2022.01); *G06V 10/993* (2022.01); *G06V 20/70* (2022.01); *H04N 23/64* (2023.01); *G06T 2207/10056* (2013.01); *G06T 2207/20084* (2013.01); *G06T 2207/30136* (2013.01); *G06T 2207/30168* (2013.01)

(58) Field of Classification Search
USPC ............................................................ 348/91
See application file for complete search history.

(56) References Cited

FOREIGN PATENT DOCUMENTS

| JP | H06-148062 A | 5/1994 |
| JP | 2004-020519 A | 1/2004 |
| JP | 2004-325358 A | 11/2004 |
| JP | 2007-204772 A | 8/2007 |
| JP | 2018-05513 A | 2/2018 |
| JP | 2018-121752 A | 8/2018 |
| JP | 2019-012037 A | 1/2019 |
| WO | 2016/038705 A1 | 3/2016 |
| WO | 2017/010397 A1 | 1/2017 |
| WO | 2019/171124 | 9/2019 |

OTHER PUBLICATIONS

F. Ajioka et al., "Development of High Accuracy Segmentation Model for Microstructure of Steel by Deep Learning," ISIJ International, vol. 60, No. 5, pp. 954-959, Jan. 2020.
D.S. Bulgarevich et al., "Automatic Steel Labeling on Certain Microstructural Constituents with Image Processing and Machine Learning Tools," Science and Technology of Advanced Materials, vol. 20, No. 1, pp. 532-542, Jun. 2019.
International Search Report dated May 18, 2021 in counterpart International Application No. PCT/JP2021/009006.
Written Opinion dated May 18, 2021 in counterpart International Application No. PCT/JP2021/009006.
Extended European Search Report dated Oct. 10, 2023, of counterpart European Patent Application No. 21782081.0.
J. Gola et al., "Advanced Microstructure Classification by Data Mining Methods," Computational Materials Science, Elsevier, vol. 148, pp. 324-335, 2018.
First Office Action dated Aug. 13, 2024, of counterpart Chinese Patent Application No. 202180025636.X, along with an English machine translation.

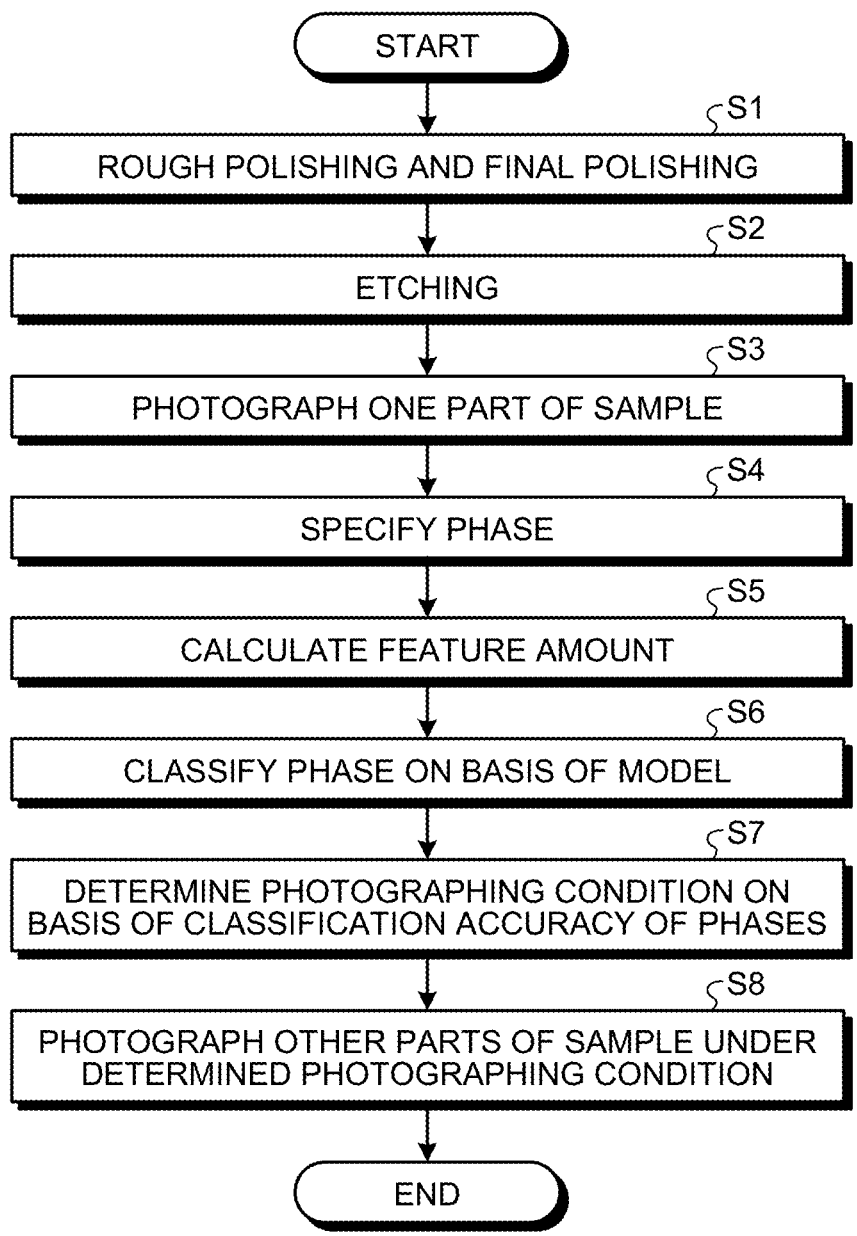

F: FERRITE PHASE
M: MARTENSITE PHASE

FERRITE PHASE    MARTENSITE PHASE

FERRITE PHASE    MARTENSITE PHASE

FIG.13
| | ORIGINAL IMAGE | CLASSIFICATION RESULT | CLASSIFICATION ACCURACY |
|---|---|---|---|
| (a) | 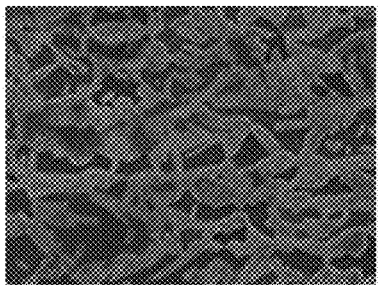 | 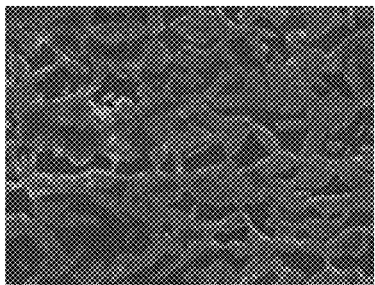 | × |
| (b) | 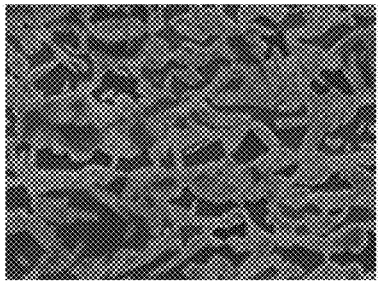 | 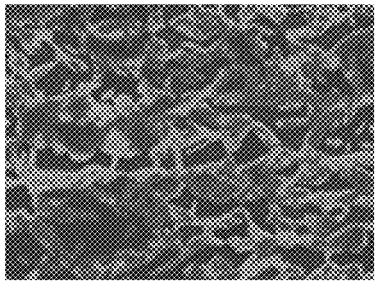 | × |
| (c) | 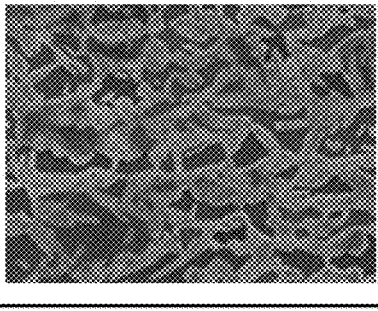 | 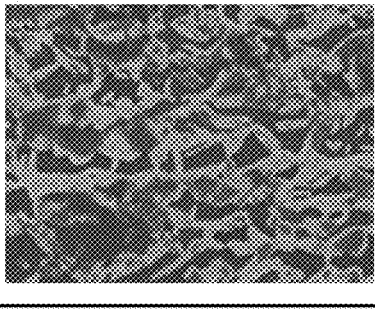 | × |
| (d) | 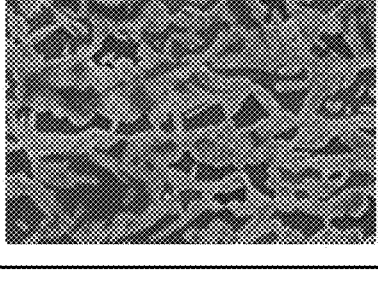 | 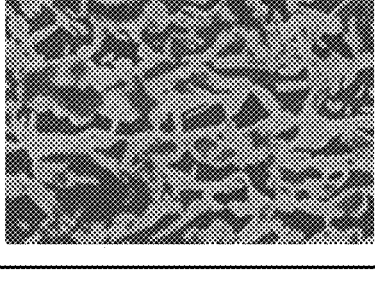 | × |
| (e) |  |  | ○ |

FIG.14
| | ORIGINAL IMAGE | CLASSIFICATION RESULT | CLASSIFICATION ACCURACY |
|---|---|---|---|
| (a) | 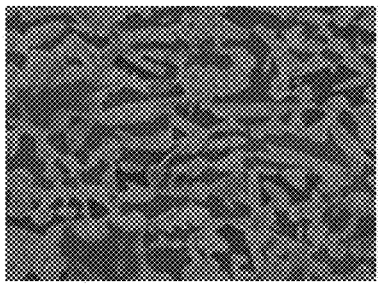 | 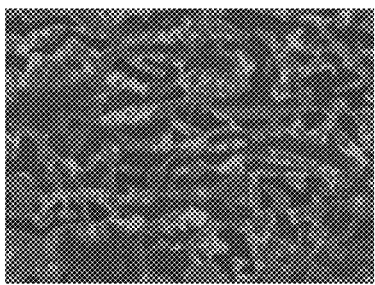 | × |
| (b) | 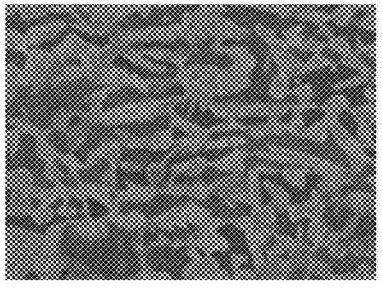 | 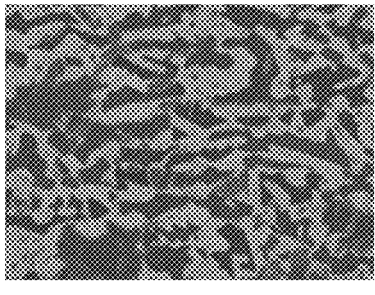 | × |
| (c) | 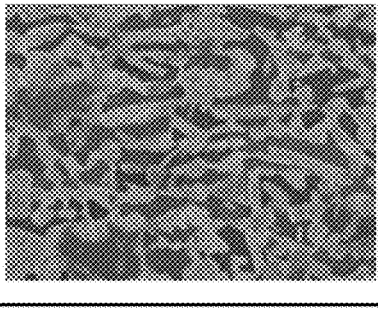 | 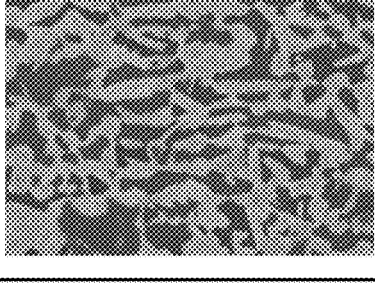 | ○ |
| (d) | 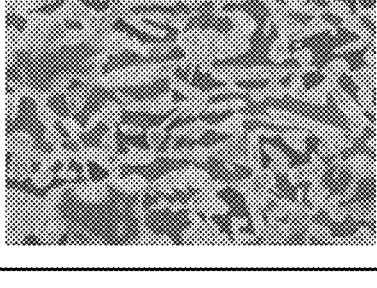 | 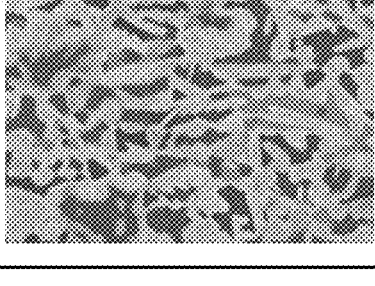 | × |
| (e) |  | 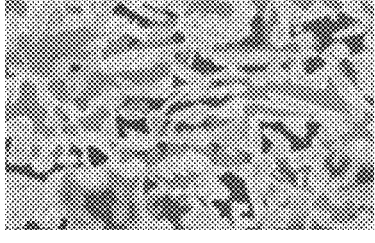 | × |

PHOTOGRAPHING CONDITION DETERMINING METHOD FOR METAL STRUCTURE, PHOTOGRAPHING METHOD FOR METAL STRUCTURE, PHASE CLASSIFICATION METHOD FOR METAL STRUCTURE, PHOTOGRAPHING CONDITION DETERMINING DEVICE FOR METAL STRUCTURE, PHOTOGRAPHING DEVICE FOR METAL STRUCTURE, PHASE CLASSIFICATION DEVICE FOR METAL STRUCTURE, MATERIAL PROPERTY ESTIMATING METHOD FOR METAL MATERIAL, AND MATERIAL PROPERTY ESTIMATING DEVICE FOR METAL MATERIAL

TECHNICAL FIELD

This disclosure relates to a photographing condition determining method for a metal structure, a photographing method for a metal structure, a phase classification method for a metal structure, a photographing condition determining device for a metal structure, a photographing device for a metal structure, a phase classification device for a metal structure, a material property estimating method for a metal material, and a material property estimating device for a metal material.

BACKGROUND

In recent years, exhaust gas regulations have been implemented to reduce discharged pollutants from the viewpoint of preserving the global environment. In addition, improvement of fuel efficiency by weight reduction of the vehicle body is strongly demanded for automobiles. One effective method of reducing the weight of the vehicle body is to increase the strength of a thin steel plate used for the vehicle body, and the amount of high-strength steel plate used in automobiles is increasing year by year.

In general, the property of a metal material such as a steel plate, significantly depends on the metal structure at the scale (mm to μm scale) of the level of an optical microscope or an electron microscope despite of the same composition. Therefore, in developing a high-strength steel plate, a method of changing the composition is used such as a method using solid solution strengthening by addition of a solid solution strengthening element or a precipitation strengthening method using a precipitate by addition of a precipitation strengthening element. Other than those methods, a method of improving the mechanical property by allowing the metal structure to be finally obtained to change by changing the heat treatment conditions with the same composition.

As described above, to develop a high-strength steel plate, it is important not only to control the composition but also to control the metal structure, and for this reason, it is important to observe a metal material with an optical microscope, an electron microscope or the like and to quantitatively evaluate the metal structure. In fact, at the site of material development, structure observation of metal materials under different heat treatment conditions is performed on a daily basis.

When a metal structure is observed by a known photographing device such as an electron microscope after sample preparation such as a known polishing method and etching method is performed on a metal material such as a steel plate, the contrast is generally different for each phase, and thus each phase can be discriminated. For example, in observing a metal structure of a dual phase steel plate (DP steel plate) including the ferrite phase and the martensite phase, which is typically used as a high tensile strength material of a steel material, first, rough polishing is performed, and then final polishing using a polishing agent of 0.05 μm to 2 μm is performed. Subsequently, etching is performed using a 0.5% to 8% nital solution. Then, when the metal structure is observed at a magnification higher than or equal to 500 times using a scanning electron microscope, the ferrite phase and the martensite phase are observed with different contrasts, and both phases can be distinguished. Depending on the heat treatment conditions, the volume fraction of each phase of the metal structure including the soft ferrite phase and the hard martensite phase or the shape of the metal structure change, and the mechanical property greatly changes. Therefore, material development that attempts to achieve mechanical property demanded as a material by controlling the volume fraction of each phase of the metal structure and the shape of the metal structure is performed on a daily basis.

To clearly derive the relationship between the mechanical property and the metal structure, it is important to accurately identify phases constituting the observed metal structure and to quantitatively evaluate the volume fraction of each of the phases and the shape of the metal structure. Generally, the act of identifying (classifying) and extracting phases from an image ("structure image") obtained by photographing a metal structure is referred to as "segmentation." However, in the conventional segmentation, a worker classifies each phase of a structure image by coloring manually. That method not only requires a huge amount of time merely to analyze one structure image but also causes a large error depending on a worker who colors manually since the recognition of a phase varies depending on the worker. Therefore, in practice, segmentation by manual coloring is hardly performed, and evaluation of a structure image is actually merely qualitative.

As a known segmentation method in place of such manual coloring that causes large errors and requires enormous amount of time, binarization of luminance values can be mentioned. In that method, a threshold value for the luminance value is determined for image data of a photographed metal structure, only a specific phase is extracted by converting an image using a computer or the like to have two colors, and the volume fraction is measured by deriving the area of each of the colors. That method can accurately perform phase classification when luminance values are clearly different for each phase of a metal structure. In addition, since only the threshold value of the luminance value is determined as a work, the metal structure can be quantitatively evaluated at a much higher speed than the above-described manual coloring. However, on the other hand, in metal materials, there are many instances where the difference in luminance value for each phase is not clear, and there are many instances where accurate classification cannot be performed due to a large error when the difference in luminance value is not clear.

In addition, even when the luminance value is clearly different for each phase, in a metal material, the luminance value changes depending on the etching time of $10^{-2}$ s order, which is difficult to control, in sample preparation performed before photographing. Therefore, there is a problem that the binarization threshold value needs to be determined for each structure image that is photographed even for the same phase. In addition to the etching conditions, for example, in an optical microscope, the luminance value of an image can be changed by changing the intensity of a light source. However, since the setting depends on the photographer, there is a problem that the binarization threshold value needs to be determined for each photographer each time.

In recent years, the performance of computers have been dramatically improved, and technology of analyzing an image without including human factors by using a more advanced calculation technology, rather than the above-described manual coloring nor simple binarization of a luminance value, has been developed. For example, JP 2018-121752 A discloses the following technology. First, an image of a part of a human body surface is converted into an image in a space of an opposite color, and each of components in the space of the opposite color of the image in the space in the opposite color is decomposed into subband images of different spatial frequencies. Then, for the subband image, a feature value corresponding to a part of the human body surface is calculated, and the appearance of the part of the human body surface is evaluated based on the feature value. By using that technology, the state, the texture, and others of the skin can be objectively and quickly evaluated from the image of the human skin.

Furthermore, WO 2017/010397 A discloses the following technology. First, a plurality of binarized images is generated by performing a plurality of times of binarization processing on one structure image obtained by photographing a structure while varying a reference value for the binarization. Subsequently, the number of hole-shaped regions is calculated for each of the plurality of binarized images, the number of features characterizing the correspondence relationship between the plurality of binarized reference values and the number of hole-shaped regions is specified, and output information corresponding to the number of features is generated.

However, the technology disclosed in JP '752 is merely for evaluating a skin structure, and thus it is difficult to apply the technology to a structure of a metal material such as a steel plate. Furthermore, it is difficult to cope with a contrast difference or the like that varies depending on etching conditions that are difficult to control. In addition, the technology disclosed in WO '397 is also for analyzing an image of living cells, and it is difficult to apply the technology to analysis of a structure image, in which the contrast greatly fluctuates depending on etching, like in a metal material.

It could therefore be helpful to provide a photographing condition determining method for a metal structure, a photographing method for a metal structure, a phase classification method for a metal structure, a photographing condition determining device for a metal structure, a photographing device for a metal structure, a phase classification device for a metal structure, a material property estimating method for a metal material, and a material property estimating device for a metal material capable of accurately classifying a phase of the metal structure even when the photographing condition varies depending on the etching condition, a photographing means, or a photographer.

SUMMARY

We thus provide a photographing condition determining method for photographing a metal structure of a metal material that includes: a photographing step of photographing a part of the metal structure of the metal material having been subjected to predetermined sample preparation under a predetermined photographing condition; a phase specification step of assigning, to pixels corresponding to one or a plurality of predetermined phases of the metal structure, labels of respective phases for an image photographed in the photographing step; a feature value calculating step of calculating one or more feature values for a pixel to which a label of one of the phases has been assigned in the phase specification step; a phase classification step of classifying the phases of the metal structure of the image by inputting a feature value calculated in the feature value calculating step to a model, which has been learned in advance using feature values assigned with labels of respective phases as input and labels of the respective phases as output, and acquiring a label of a phase of a pixel corresponding to the feature value that has been input; and a photographing condition determining step of determining a photographing condition when other parts of the metal structure are photographed based on a classification result of the phase classification step.

Moreover, in the above-described photographing condition determining method for a metal structure, in the photographing step, a part of the metal structure is photographed under a plurality of predetermined photographing conditions, and in the photographing condition determining step, a photographing condition with which a classification accuracy of the phases in the phase classification step is the highest among the plurality of photographing conditions used in the photographing step is determined as a photographing condition for photographing the other parts of the metal structure.

We also provide a photographing condition determining method for photographing a metal structure of a metal material that includes: a photographing step of consecutively photographing a part of the metal structure having been subjected to predetermined sample preparation while a photographing condition is varied; a feature value calculating step of calculating one or more feature values for images photographed in the photographing step; a phase classification step of classifying phases of the metal structure of the image by inputting a feature value calculated in the feature value calculating step to a model, which has been learned in advance using feature values of pixels assigned with labels of one or a plurality of predetermined phases of the metal structure as input and labels of the respective phases as output, and acquiring a label of a phase of a pixel corresponding to the feature value that has been input; and a photographing condition determining step of determining a photographing condition when other parts of the metal structure are photographed from among a plurality of photographing conditions used in the photographing step based on a classification result of the phase classification step.

Moreover, in the above-described photographing condition determining method for a metal structure, in the photographing condition determining step, a photographing condition under which a classification accuracy of the phases in the phase classification step is the highest among the photographing conditions used in the photographing step is determined as a photographing condition for photographing the other parts of the metal structure.

Moreover, in the above-described photographing condition determining method for a metal structure, the photographing condition includes at least one of a contrast value, a brightness value, and an intensity of a light source.

Moreover, the above-described photographing condition determining method for a metal structure further includes, before the photographing step: a polishing step of roughly polishing the metal material and then performing buffing using a polishing material of 0.05 μm to 2 μm; and an etching step of etching the metal material using a nital solution which is prepared by mixing ethanol and nitric acid and has a nitric acid concentration of 0.5% to 8%.

We further provide a photographing method for a metal structure that photographs the other parts of the metal structure of the metal material under the photographing condition determined by the photographing condition determining method after the photographing condition determining method for a metal structure.

We still further provide a phase classification method for a metal structure that includes the steps of: photographing the metal structure by the photographing method for a metal structure; and classifying phases of the metal structure.

We yet further provide a photographing condition determining device for photographing a metal structure of a metal material that includes: a photographing unit that photographs a part of the metal structure of the metal material having been subjected to predetermined sample preparation under a predetermined photographing condition; a phase specification unit that assigns, to pixels corresponding to one or a plurality of predetermined phases of the metal structure, labels of respective phases for an image photographed by the photographing unit; a feature value calculating unit that calculates one or more feature values for a pixel to which a label of one of the phases has been assigned by the phase specification unit; a phase classification unit that classifies the phases of the metal structure of the image by inputting a feature value calculated by the feature value calculating unit to a model, which has been learned in advance using feature values assigned with labels of respective phases as input and labels of the respective phases as output, and acquiring a label of a phase of a pixel corresponding to the feature value that has been input; and a photographing condition determining unit that determines a photographing condition when other parts of the metal structure are photographed based on a classification result of the phase classification unit.

We still yet further provide a photographing condition determining device for photographing a metal structure of a metal material that includes: a photographing unit that consecutively photographs a part of the metal structure having been subjected to predetermined sample preparation while a photographing condition is varied; a feature value calculating unit that calculates one or more feature values for images photographed by the photographing unit; a phase classification unit that classifies phases of the metal structure of the image by inputting a feature value calculated in the feature value calculating unit to a model, which has been learned in advance using feature values of pixels assigned with labels of one or a plurality of predetermined phases of the metal structure as input and labels of the respective phases as output, and acquiring a label of a phase of a pixel corresponding to the feature value that has been input; and a photographing condition determining unit that determines a photographing condition when the other parts of the metal structure are photographed from among a plurality of photographing conditions used in the photographing unit based on a classification result of the phase classification unit.

We also provide a photographing device for a metal structure that photographs the other parts of the metal structure of the metal material under the photographing condition determined by the photographing condition determining device.

We further provide a phase classification device for a metal structure that photographs the metal structure by the photographing device for a metal structure, and classifies phases of the metal structure.

We yet further provide a material property estimating method for a metal material for estimating a material property of the metal material that includes, after the phase classification method for a metal structure: a quantitative evaluation step of calculating a quantitative evaluation value of the metal structure by calculating a size, an area ratio, or a shape of each of the classified phases; a data selection step of selecting data to be used for estimation of a material property of the metal material from the quantitative evaluation value and material properties of the metal material prepared in advance; a model generating step of generating an estimation model for estimating a material property of the metal material using the data that has been selected; and a material property estimating step of estimating a material property of the metal material using the estimation model that has been generated.

We still further provide a material property estimating device for a metal material for estimating a material property of the metal material that includes: an input unit that inputs an image in which phases of a metal structure have been classified; a quantitative evaluation unit that calculates a quantitative evaluation value of the metal structure by calculating a size, an area ratio, or a shape of each of the classified phases; a data recording unit that records the quantitative evaluation value in a database; a data selection unit that selects data to be used for estimation of a material property of the metal material from among the quantitative evaluation value and material properties of the metal material recorded in the database; a model generation unit that generates an estimation model for estimating a material property of the metal material using the data that has been selected; a material property estimating unit that estimates a material property of the metal material using the estimation model that has been generated; and an output unit that outputs the material property of the metal material that has been estimated.

According to a photographing condition determining method for a metal structure, a photographing method for a metal structure, a phase classification method for a metal structure, a photographing condition determining device for a metal structure, a photographing device for a metal structure, and a phase classification device for a metal structure, the following effects are obtained. That is, in segmentation for classifying important phases of a metal structure that greatly affect various material properties such as the mechanical property or the corrosion property, the phases of the metal structure can be accurately classified even when the photographing condition varies depending on the etching condition, the photographing means, or the photographer. It is also possible to determine photographing conditions under which quantitative evaluation can be performed.

In addition, according to a material property estimating method for a metal material and a material property estimating device for a metal material, quantitative evaluation can be efficiently performed from the classification result of the phases of the metal structure. Therefore, by deriving a correlation between the quantitative evaluation value and the material properties of the metal material, the material properties of the metal material can be accurately estimated. As a result, the material properties of the metal material can be grasped at the same time as the image of the metal structure is viewed, and thus the efficiency of development of a metal material (for example, a steel plate) can be improved.

BRIEF DESCRIPTION OF THE DRAWINGS

FIG. 2 is a flowchart illustrating a flow of a photographing condition determining method and a photographing method according to the first example.

FIG. 13 is a diagram illustrating an example of the photographing condition determining method and the photographing method according to the second example and illustrating structure images consecutively photographed while the contrast value is changed in a first photographing step for a sample prepared by a method A and phase classification images corresponding to the structure images.

FIG. 14 is a diagram illustrating an example of the photographing condition determining method and the photographing method according to the second example and illustrating structure images consecutively photographed while the contrast value is changed in a first photographing step for a sample prepared by a method B and phase classification images corresponding to the structure images.

Figure 1:
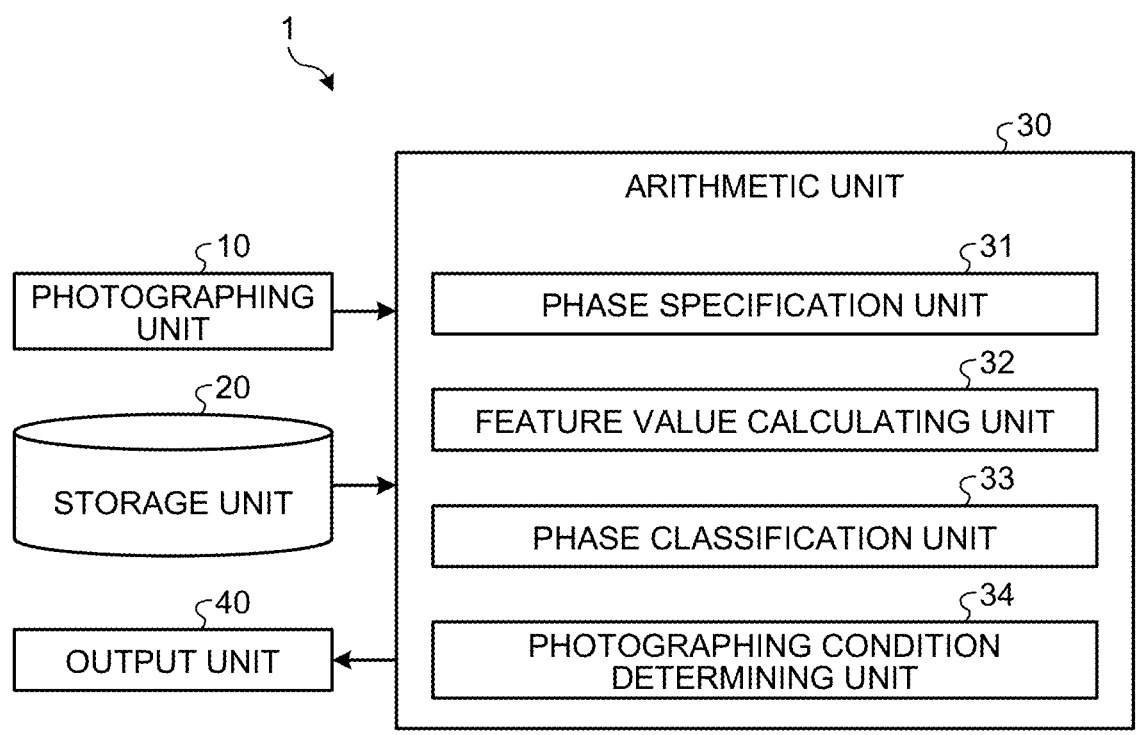
FIG. 1 is a block diagram illustrating a schematic configuration of a photographing condition determining device and a photographing device for a metal structure according to a first example.

REFERENCE SIGNS LIST 1, 1A PHOTOGRAPHING CONDITION DETERMINING DEVICE
3 MATERIAL PROPERTY ESTIMATING DEVICE
10 PHOTOGRAPHING UNIT
20 STORAGE UNIT
30 ARITHMETIC UNIT
31 PHASE SPECIFICATION UNIT
32 FEATURE VALUE CALCULATING UNIT
33 PHASE CLASSIFICATION UNIT
34 PHOTOGRAPHING CONDITION DETERMINING UNIT
40 OUTPUT UNIT
50 ARITHMETIC UNIT
51 FEATURE VALUE CALCULATING UNIT
52 PHASE CLASSIFICATION UNIT
53 PHOTOGRAPHING CONDITION DETERMINING UNIT
70 INPUT UNIT
80 OUTPUT UNIT
90 ARITHMETIC UNIT
91 QUANTITATIVE EVALUATION UNIT
92 DATA RECORDING UNIT
93 DATA SELECTION UNIT
94 MODEL GENERATION UNIT
95 MATERIAL PROPERTY ESTIMATING UNIT
100 STORAGE UNIT

DETAILED DESCRIPTION

First Example

A photographing condition determining method for a metal structure, a photographing method for a metal structure, a phase classification method for a metal structure, a photographing condition determining device for a metal structure, a photographing device for a metal structure, and a phase classification device for a metal structure according to a first example will be described with reference to FIGS. 1 and 2.

The photographing condition determining method and the photographing condition determining device for a metal structure according to the example are a method and a device for determining the photographing condition of the metal structure when learning a phase of the metal structure, which is important information in controlling the property of a metal material used as a material of various products such as a structural member and an automobile member. In addition, the photographing method and the photographing device for a metal structure according to the example are a method and a device for photographing the metal structure under the photographing condition determined by the photographing condition determining method and the photographing condition determining device.

A metal material is, for example, a DP steel plate including the ferrite phase and the martensite phase. Hereinafter, the configurations of the photographing condition determining device and the photographing device for a metal structure will be described, and then the photographing condition determining method, the photographing method, and a model generation method using these devices will be described. Then, the configuration of a material property estimating device for a metal material will be described, and then a material property estimating method using the device will be described.

Photographing Condition Determining Device/Photographing Device

A photographing condition determining device for a metal structure ("photographing condition determining device") 1 will be described with reference to FIG. 1. The photographing condition determining device 1 includes a photographing unit 10, a storage unit 20, an arithmetic unit 30, and an output unit 40. The photographing device according to this example is implemented by the same configuration as that of the photographing condition determining device 1 illustrated in the drawing.

The photographing unit 10 is a means that photographs a structure image of a metal material and inputs the structure image to the arithmetic unit 30. The photographing unit 10 includes, for example, a known photographing device such as an optical microscope or a scanning electron microscope widely used to photograph a structure image.

The storage unit 20 includes a recording medium such as an erasable programmable ROM (EPROM), a hard disk drive (HDD), a solid state drive (SSD), or a removable medium. Examples of the removable medium include a universal serial bus (USB) memory and a disk recording medium such as a compact disc (CD), a digital versatile disc (DVD), or a Blu-ray (registered trademark) (BD) disc. Furthermore, the storage unit 20 can store an operating system (OS), various programs, various tables, various databases and the like.

The storage unit 20 stores, for example, a database of feature values calculated by a feature value calculating unit 32, a model (learned model) learned in advance using feature values assigned with labels of each phase as input and labels of each phase as output, and others. A method of generating this model will be described later.

The arithmetic unit 30 is implemented by, for example, a processor including a central processing unit (CPU) or the like and a memory (main storage unit) including a random access memory (RAM), a read only memory (ROM), or the like. The arithmetic unit 30 implements a function matching a predetermined purpose by loading a program into a work area of the main storage unit and executing the program and controlling each component or the like through the execution of the program. The arithmetic unit 30 functions as a phase specification unit 31, the feature value calculating unit 32, a phase classification unit 33, and a photographing condition determining unit 34 through execution of a program described above. Details of each unit will be described later.

The output unit 40 is an output means that outputs an arithmetic result by the arithmetic unit 30. The output unit 40 includes, for example, a display, a printer, a smartphone or the like. The output unit 40 outputs, for example, a phase of a metal structure specified by the phase specification unit 31, a feature value of the phase of the metal structure calculated by the feature value calculating unit 32, a classification result of the phase of the metal structure by the phase classification unit 33, photographing conditions determined by the photographing condition determining unit 34, and others. An output format by the output unit 40 is not particularly limited and may be, for example, data such as a text file or an image file, or the output may be in a mode of projection to an output device.

Photographing Condition Determining Method/Photographing Method

The photographing condition determining method using the photographing condition determining device 1 and a photographing method using the photographing device will be described with reference to FIG. 2. In the photographing condition determining method, a polishing step S1, an etching step S2, a first photographing step S3, a phase specification step S4, a feature value calculating step S5, a phase classification step S6, and a photographing condition determining step S7 are performed in the order mentioned. In the photographing method, a second photographing step S8 is performed after the steps of the photographing condition determining method. Each of the steps will be described below.

Polishing Step S1

In the polishing step S1, rough polishing and final polishing are sequentially performed on the metal material to be observed. In the rough polishing, for example, a commercially available sandpaper obtained by applying abrasive grains to paper is used to remove scratches visible at the naked eye level. Subsequently, in the final polishing, buffing using a polishing material of 0.05 μm to 2 μm is performed. As the polishing agent, for example, a known polishing agent such as diamond or silica can be used. In addition, in the final polishing, for example, buffing is performed until no flaws can be seen when observed with an optical microscope at a magnification of 10 times to 500 times. In addition, if a large number of polishing scratches remain, etching unevenness is caused, which causes an error in phase classification, and thus polishing is performed not to leave scratches as much as possible. In the final polishing, buffing is preferably performed so that no scratches are visible when observed with an optical microscope at a magnification at less than or equal to 1000 times.

Etching Step S2

In the metal material, the amount of corrosion varies depending on phases such as the ferrite phase and the martensite phase, and thus, by performing etching, contrast can be obtained for each phase, thereby allowing the phases to be classified. In the etching step S2, a nital solution having a nitric acid concentration of 0.5% to 8%, which is prepared by mixing ethanol and nitric acid, is used, and the metal material (sample) is immersed in the nital solution for 0.5 s to 10.0 s and then rinsed with distilled water.

In the etching step S2, instead of immersing the metal material in the nital solution, the nital solution may be sprayed onto the metal material by a sprayer, and the metal material may be rinsed with distilled water after 0.5 s to 10.0 s has elapsed. In the etching step S2, instead of immersing the metal material in the nital solution, the nital solution may be attached to the metal material using a soft cloth such as gauze, and the metal material may be rinsed with distilled water after 0.5 s to 10.0 s has elapsed. In the etching step S2, it is preferable that the etching is performed under the condition that the difference in nitric acid concentration from an etching solution in the etching step when a model has been generated is less than 0.1% and that the difference in immersion time is less than 2.0 s. With this condition, the classification accuracy in the phase classification step S6 to be described later can be improved (classification error can be reduced).

First Photographing Step S3

In the first photographing step S3, the photographing unit 10 photographs a part of the metal structure (a field of view of a part of the metal structure) of the metal material having been subjected to predetermined sample preparation (the polishing step S1 and the etching step S2) under a predetermined photographing condition. The "photographing condition" includes a contrast value and a brightness value when the photographing unit 10 is a scanning electron microscope and includes the intensity of a light source when the photographing unit 10 is an optical microscope.

Specifically, in the first photographing step S3, a part of the metal structure is photographed under a plurality of predetermined photographing conditions. That is, when the photographing unit 10 is a scanning electron microscope, a plurality of images of the same part of the metal structure is photographed while the contrast value or the brightness value is varied. In addition, when the photographing unit 10 is an optical microscope, a plurality of images of the same part of the metal structure is photographed while the intensity of the light source is varied.

Phase Specification Step S4

In the phase specification step S4, for the structure image photographed in the first photographing step S3, the phase specification unit 31 specifies phases by assigning labels of the respective phases to pixels corresponding to one or a plurality of predetermined phases of the metal structure. "To assign labels of the respective phases to pixels of the phases in the structure image" means that, for example, in a DP steel plate, pixels corresponding to the ferrite phase and the martensite phase are specified in the structure image, and that the pixels of the structure image are associated with the ferrite phase and the martensite phase (see FIG. 8). Specification of each phase may be performed by specifying a plurality of points from pixel to pixel of the structure image or may be specified by an area by encircling with a size of about the size of a crystal grain. In addition, in the phase specification step S4, it is preferable to specify two or more regions for each phase by area to improve the classification accuracy of phases (reduce the classification error) in the second photographing step S8 to be described later.

Feature Value Calculating Step S5

In the feature value calculating step S5, the feature value calculating unit 32 calculates one or more feature values for a pixel to which a label of one of the phases has been assigned in the phase specification step S4. For example, one or more feature values among feature values (1) to (8) are calculated.

(1) Identity Feature Value

An identity feature value is a feature value indicating the luminance value itself of the structure image.

(2) Mean Feature Value

A mean feature value indicates an average value of luminance values in a predetermined area of the structure image. That is, the mean feature value is obtained by extracting the predetermined area "x pixels×y pixels" from each of the phases of the structure image and averaging luminance values in the area. The "number of pixels x" and the "number of pixels y" may be the same or different. In addition, the "number of pixels x" and the "number of pixels y" are, for example, preferably larger than noise included in the structure image and are in an area including a size of less than ½ of the crystal grain size of a smaller crystal grain size among the plurality of phases of the metal structure. Moreover, when there is anisotropy, it is preferable to set to a size of about the crystal grain size in each of an x direction and a y direction. Furthermore, the region of x pixels×y pixels does not need to be rectangular and, for example, when the structure image has a spherical shape, the region of x pixels×y pixels is also preferably spherical. Furthermore, the mean feature value may be calculated for a plurality of numbers of pixels x and y. When the area of pixels is too large, the influence of the grain boundary and the influence of another adjacent phase are received. Therefore, the area of pixels preferably includes a size of less than ½ of the crystal grain size of a larger crystal grain size.

Figure 3A:
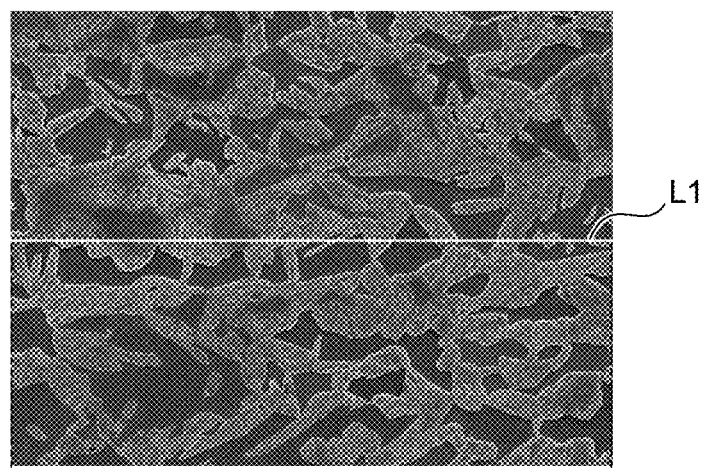
FIG. 3 is a diagram illustrating (FIG. 3(a)) a photograph of a DP steel plate structure taken using a scanning electron microscope and (FIG. 3(b)) a luminance value profile on line L1.
Figure 3B:
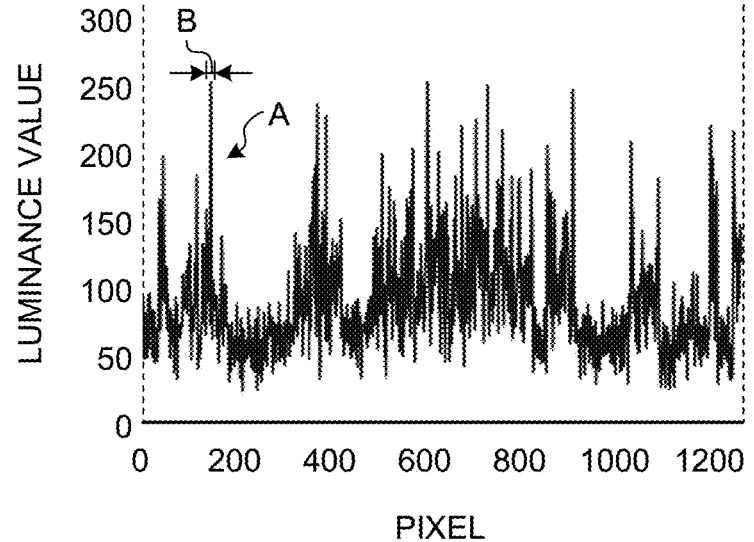

The "noise included in the structure image" indicates, for example, a part where the luminance value is locally large in the structure image (for example, see portion A in (b) of FIG. 3). Moreover, "the number of pixels x and y are larger than noise" indicates that the area is made larger than the width of the noise (see portion B in (b) of the drawing). (a) of FIG. 3 is a diagram illustrating the structure image (original image) photographed with a scanning electron microscope, and (b) is a diagram illustrating a line profile of the luminance value in the central part (position of line L1) of the structure image.

(3) Gaussian Feature Value

A Gaussian feature value indicates an average value of luminance values whose weight is increased toward the center in the predetermined area of the structure image. That is, the Gaussian feature value is obtained by extracting the predetermined area "x pixels×y pixels" from each of the phases of the structure image and extracting an average value in which the weight is increased toward the central pixel. The "number of pixels x" and the "number of pixels y" may be the same or different. In addition, the "number of pixels x" and the "number of pixels y" are, for example, preferably larger than noise included in the structure image and are in an area including a size of less than ½ of the crystal grain size of a smaller crystal grain size among the plurality of phases of the metal structure. Moreover, when there is anisotropy, it is preferable to set to a size of about the crystal grain size in each of an x direction and a y direction. Furthermore, the region of x pixels×y pixels does not need to be rectangular and, for example, when the structure image has a spherical shape, the region of x pixels×y pixels is also preferably spherical. Furthermore, the Gaussian feature value may be calculated for a plurality of numbers of pixels x and y. When the area of pixels is too large, the influence of the grain boundary and the influence of another adjacent phase are received. Therefore, the area of pixels preferably includes a size of less than ½ of the crystal grain size of a larger crystal grain size.

In addition, when the Gaussian feature value is calculated, how much weight is given to the central pixel can be set by a worker as desired. However, it is preferable to use the Gaussian function shown in Expression (1):

$$A \cdot \exp(-(\Delta x^2 + \Delta y^2)) \qquad (1).$$

$\Delta x$ and $\Delta y$ in Expression (1) can be expressed as Equations (2) and (3):

$$\Delta x = x_i - x_c$$

$$\Delta y = y_i - y_c \qquad (2)$$

where, $x_c, y_c$: central coordinates of square, and $$x_i, y_i: \text{position coordinates of square} \qquad (3).$$

(4) Median Feature Value

A median feature value indicates a median value of luminance values in the predetermined area of the structure image. That is, the median feature value is obtained by extracting the predetermined area "x pixels×y pixels" from each of the phases of the structure image and extracting the median value of luminance values in the area. The "number of pixels x" and the "number of pixels y" may be the same or different. In addition, the "number of pixels x" and the "number of pixels y" are, for example, preferably larger than noise included in the structure image and are in an area including a size of less than ½ of the crystal grain size of a smaller crystal grain size among the plurality of phases of the metal structure. Moreover, when there is anisotropy, it is preferable to set to a size of about the crystal grain size in each of an x direction and a y direction. Furthermore, the region of x pixels×y pixels does not need to be rectangular and, for example, when the structure image has a spherical shape, the region of x pixels×y pixels is also preferably spherical. Furthermore, the median feature value may be calculated for a plurality of number of pixels x and y. When the area of pixels is too large, the influence of the grain boundary and the influence of another adjacent phase are received. Therefore, the area of pixels preferably includes a size of less than ½ of the crystal grain size of a larger crystal grain size.

(5) Max Feature Value

A max feature value indicates the maximum value of luminance values in the predetermined area of the structure image. That is, the max feature value is obtained by extracting the predetermined area "x pixels×y pixels" from each of the phases of the structure image and extracting the maximum value of the luminance values in the area. The "number of pixels x" and the "number of pixels y" may be the same or different. In addition, the "number of pixels x" and the "number of pixels y" are, for example, preferably larger than noise included in the structure image and are in an area including a size of less than ½ of the crystal grain size of a smaller crystal grain size among the plurality of phases of the metal structure. Moreover, when there is anisotropy, it is preferable to set to a size of about the crystal grain size in each of an x direction and a y direction. Furthermore, the region of x pixels×y pixels does not need to be rectangular and, for example, when the structure image has a spherical shape, the region of x pixels×y pixels is also preferably spherical. Furthermore, the max feature value may be calculated for a plurality of numbers of pixels x and y. When the area of pixels is too large, the influence of the grain boundary and the influence of another adjacent phase are received. Therefore, the area of pixels preferably includes a size of less than ½ of the crystal grain size of a larger crystal grain size.

(6) Min Feature Value

A min feature value indicates the minimum value of luminance values in the predetermined area of the structure image. That is, the min feature value is obtained by extracting the predetermined area "x pixels×y pixels" from each of the phases of the structure image and extracting the minimum value of luminance values in the area. The "number of pixels x" and the "number of pixels y" may be the same or different. In addition, the "number of pixels x" and the "number of pixels y" are, for example, preferably larger than noise included in the structure image and are in an area including a size of less than ½ of the crystal grain size of a smaller crystal grain size among the plurality of phases of the metal structure. Moreover, when there is anisotropy, it is preferable to set to a size of about the crystal grain size in each of an x direction and a y direction. Furthermore, the region of x pixels×y pixels does not need to be rectangular and, for example, when the structure image has a spherical shape, the region of x pixels×y pixels is also preferably spherical. Furthermore, the min feature value may be calculated for a plurality of numbers of pixels x and y. When the area of pixels is too large, the influence of the grain boundary and the influence of another adjacent phase are received. Therefore, the area of pixels preferably includes a size of less than ½ of the crystal grain size of a larger crystal grain size.

(7) Derivative Feature Value

A derivative feature value is obtained by extracting the predetermined area "x pixels×y pixels" from each of the phases of the structure image and calculating differential values in the x direction and the y direction for pixels at ends of the area, and the feature value is calculated for each of the directions. The "number of pixels x" and the "number of pixels y" may be the same or different. In addition, the "number of pixels x" and the "number of pixels y" are, for example, preferably larger than noise included in the structure image and are in an area including a size of less than ½ of the crystal grain size of a smaller crystal grain size among the plurality of phases of the metal structure. Moreover, when there is anisotropy, it is preferable to set to a size of about the crystal grain size in each of an x direction and a y direction. Furthermore, the region of x pixels×y pixels does not need to be rectangular and, for example, when the structure image has a spherical shape, the region of x pixels×y pixels is also preferably spherical, and it is desirable to calculate differential values in a plurality of directions. Furthermore, the derivative feature value may be calculated for a plurality of numbers of pixels x and y. When the area of pixels is too large, the influence of the grain boundary and the influence of another adjacent phase are received. Therefore, the area of pixels preferably includes a size of less than ½ of the crystal grain size of a larger crystal grain size.

(8) Derivative Addition Feature Value

A derivative addition feature value is obtained by adding derivative feature values in one direction or a plurality of directions by calculating, for the derivative feature value described above, the mean feature value, the Gaussian feature value, the median feature value, or either the max feature value or the min feature value, or a plurality of feature values selected therefrom. The "number of pixels x" and the "number of pixels y" described above may be the same or different. In addition, the "number of pixels x" and the "number of pixels y" are, for example, preferably larger than noise included in the structure image and are in an area including a size of less than ½ of the crystal grain size of a smaller crystal grain size among the plurality of phases of the metal structure. Moreover, when there is anisotropy, it is preferable to set to a size of about the crystal grain size in each of an x direction and a y direction. Furthermore, the region of x pixels×y pixels does not need to be rectangular and, for example, when the structure image has a spherical shape, the region of x pixels×y pixels is also preferably spherical. Furthermore, the derivative addition feature value may be calculated for a plurality of numbers of pixels x and y. When the area of pixels is too large, the influence of the grain boundary and the influence of another adjacent phase are received. Therefore, the area of pixels preferably includes a size of less than ½ of the crystal grain size of a larger crystal grain size.

Since the above feature values (1) to (8) are calculated for a large number of pixels of each of the phases, even the same phase has different feature values, and a histogram of the feature values can be created for each of the phases. Moreover, all of the above feature values (1) to (8) may be calculated, or only some of the feature values may be calculated. Furthermore, a feature value obtained by combining operations of the feature values may be added, and a feature value not listed above may be added as necessary. These selections are preferably made by a worker so that the classification accuracy of phases is improved, and feature values having a large difference between phases are preferably adopted.

When the above feature values (1) to (8) are calculated, a feature value is calculated by extracting the predetermined area "x pixels×y pixels" and that a feature value convoluted with respect to the central pixel of the "x pixels×y pixels" is calculated. Then, feature values at each position are calculated while the "x pixels×y pixels" are moved on the structure image. Furthermore, when the "x pixels×y pixels" are located at an end (upper, lower, left, or right end) on the structure image, a boundary condition is imposed, or the pixels are limited to an area from the center to the end to calculate the feature value. Furthermore, as the boundary condition, it is assumed that a pixel outside the center of "x pixels×y pixels" has the same feature value as that of the center of the "x pixels×y pixels." Alternatively, the feature values are calculated by extrapolation using an interpolation function such as a linear function, an exponential function, or a spline function from the center toward the outside.

Phase Classification Step S6

In the phase classification step S6, the phase classification unit 33 performs segmentation using a model (for example, a decision tree) generated in advance. That is, in the phase classification step S6, the feature values calculated in the feature value calculating step S5 are input to the model (for example, a decision tree) learned in advance using feature values assigned with labels of phases as input and labels of the phases as output. Then, by acquiring a label of a phase of a pixel corresponding to the feature values that have been input, a phase of the metal structure of the structure image is classified.

Photographing Condition Determining Step S7

In the photographing condition determining step S7, the photographing condition determining unit 34 determines the photographing condition for photographing other parts of the metal structure (the other field of view of the metal structure) that are different from the part photographed in the first photographing step S3 based on the classification result of the phase classification step S6. Specifically, in the photographing condition determining step S7, a photographing condition under which the classification accuracy of each of the phases in the phase classification step S6 is the highest among the plurality of photographing conditions used in the first photographing step S3 is determined as the photographing condition for photographing other parts of the metal structure.

In the photographing condition determining step S7, for example, the photographing condition is determined so that a weighted averaged correct answer rate, which is obtained by performing predetermined weighting on each of correct answer rates of the two phases (the ferrite phase and the martensite phase), is maximized. When the correct answer rate of one of the two phases is more emphasized, a weight given to the correct answer rate of that phase is increased. Alternatively, when the correct answer rates of the both phases are made equal, the weights given to the correct answer rates of the both phases are set to the same value.

In the photographing condition determining step S7, such a photographing condition under which the phase specified in the phase specification step S4 is classified with an accuracy higher than or equal to 80%. Preferably, such a photographing condition under which the classification is performed with an accuracy higher than or equal to 95% is selected. In the phase classification, a method other than the method of classifying using the model including the decision tree described above may be used. For example, the phase classification may be performed by calculating an inner product of feature vectors including feature values.

Second Photographing Step S8

In the second photographing step S8, the photographing unit 10 photographs other parts of the metal structure under the photographing condition determined in the photographing condition determining step S7. With the above, the flow ends. After the second photographing step S8, for example, the phase classification step S6 described above is performed on the photographed structure image, and the phases of the metal structure of the structure image are classified.

After the feature value calculating step S5 is performed, the calculation result of the feature values may be output from the output unit 40. The output format at that point is not particularly limited, and the output may be performed in either format of a text file (for example, a set of numerical values) or an image file (for example, a histogram image or a structure image indicating feature values). Alternatively, the classification result of the phases may be output from the output unit 40 after the phase classification step S6 is performed. The output format at that point is not particularly limited, and output may be performed in either format of a text file or an image file (for example, an image obtained by color-coding the classified phases in the structure image ("phase classification image")). In addition, the phase classification image may be output from the output unit 40 in superposition with the structure image photographed in the first photographing step S3 or in parallel with the structure image.

Model Generation Method

A method of generating a model used in the phase classification step S6 of the photographing condition determining method and the photographing method will be described. This model is only required to be generated in advance before the above-described photographing condition determining method and photographing method are performed. In the model generation method, a polishing step, an etching step, a photographing step, a phase specification step, a feature value calculating step, and a model generating step are performed in this order. Specific methods of the polishing step, the etching step, the photographing step, the phase specification step, and the feature value calculating step are similar to the respective steps of the photographing condition determining method described above.

In the polishing step and the etching step, a metal material having the same types of phases as those of the metal material to be observed ("observation sample") is polished and etched in the same manner as much as possible as that for the metal material to be observed. In the etching step, it is preferable that the etching is performed under the condition that the difference in nitric acid concentration from an etching solution in the etching step S2 is less than 0.1% and that the difference in immersion time is less than 2.0 s. With this condition, the classification accuracy of the phases in the phase classification step S6 described above can be improved (classification error can be reduced).

In the photographing step, the metal structure of the metal material is photographed. In the phase specification step, for the structure image photographed in the photographing step, phases are specified by assigning labels of the respective phases to pixels corresponding to one or a plurality of predetermined phases of the metal structure. In the feature value calculating step, one or more feature values out of the feature values (1) to (8) are calculated for a pixel to which a label of one of the phases has been assigned in the phase specification step, and a database, in which the feature values of each of the phases of the metal structure are accumulated, is configured.

In the model generating step, a model is generated through learning (machine learning) by using feature values (feature values for each of the phases of the metal structure accumulated in the database) calculated in the feature value calculating step for the pixels to which the labels of the respective phases are assigned as input and a label of each phase as an output. Specifically, in the model generating step, a decision tree in which feature values are set as a branch condition is generated. The machine learning method in the model generating step is not limited to a decision tree and may be, for example, a random forest, a neural network, or the like. However, in this example, a decision tree will be described as an example.

Specifically, in the model generating step, binarization is repeated a plurality of times from the feature values of each of the phases calculated in the feature value calculating step, thereby classifying the phases of the metal structure. In this example, from a phase specified by the worker and the feature values of each of the phases calculated in the feature value calculating step, how accurate the classification of each of the phases is to be performed is set in advance, and branching by binarization is learned based on the set numerical information.

For example, when branching of binarization is set to be performed with an accuracy of 80%, a decision tree is created by repeatedly learning a plurality of times of binarization of feature values so that classification of phases is performed with a probability higher than or equal to 80% from the specified phases and feature values thereof. The accuracy may be set by the worker as desired. However, the lower limit is preferably higher than or equal to 80%. When the accuracy is less than 80%, the classification accuracy decreases. Conversely, if the accuracy is made too high, the classification accuracy is rather deteriorated in image classification after the learning due to over-learning. Therefore, the upper limit of the accuracy is preferably less than 99%.

In the model generating step, the order of binarization (order of branching) of each feature value when binarization is performed a plurality of times may be specified in advance by the worker or may be randomly determined using random numbers. Since the desired order of binarization of the feature values is often unknown in advance, it is preferable to cause a computer to search for the order of binarization of the feature values that can be classified with an accuracy higher than or equal to the above accuracy using random numbers. Similarly, since the desired number of times of binarization of the feature values is often unknown in advance, it is preferable to cause a computer to search for the number of times of binarization of the feature values that can be classified with an accuracy higher than or equal to the above accuracy. In addition, a feature value used as a branching condition at the time of binarization may be used a plurality of times as the branching condition.

Phase Classification Method

In the phase classification method for a metal structure according to this example, the metal structure is photographed by the photographing method described above, and metal structure phases of the metal structure are classified. The phase classification device that executes the phase classification method may be implemented by the same configuration as that of the photographing condition determining device 1 or may be implemented by a configuration different from that of the photographing condition determining device 1.

According to the photographing condition determining method for a metal structure, the photographing method for a metal structure, the phase classification method for a metal structure, the photographing condition determining device 1 for a metal structure, the photographing device for a metal structure, and the phase classification device for a metal structure as described above, the following effects are achieved. That is, in segmentation for classifying important phases of a metal structure that greatly affect various material properties such as the mechanical property or the corrosion property, the phases of the metal structure can be accurately classified even when the photographing condition varies depending on the etching condition, the photographing means, or the photographer. It is also possible to determine photographing conditions under which quantitative evaluation can be performed.

In the photographing condition determining method for a metal structure, the photographing method for a metal structure, the phase classification method for a metal structure, the photographing condition determining device 1 for a metal structure, the photographing device for a metal structure, and the phase classification device for a metal structure according to this example, the following processing is performed in photographing the structure image of the metal material after sample preparation. First, a plurality of phases to be classified is specified in advance, and a specified region is automatically adjusted to have photographing conditions (for example, the contrast value) under which classification can be accurately performed based on a model prepared in advance. Then, by photographing the remaining metal material under the photographing conditions adjusted as described above, it becomes possible to cope with a difference in contrast value that fluctuates due to a slight change in etching conditions.

Furthermore, even when the photographer or the photographing means is different, segmentation can be automatically and accurately performed. For example, in the conventional method, at the time of observing an observation sample, segmentation cannot be performed with high accuracy unless polishing and etching are performed under the same conditions as those at the time when the model has been generated. On the other hand, by using our methods, segmentation can be accurately performed even when the polishing or etching conditions at the time of model generation are not followed. As a result, it is not necessary to reproduce the polishing and etching conditions that are difficult to control, and it is possible to efficiently classify a structure image.

The photographing condition determining method for a metal structure, the photographing method for a metal structure, the phase classification method for a metal structure, the photographing condition determining device 1 for a metal structure, the photographing device for a metal structure, and the phase classification device for a metal structure according to this example can accurately perform the phase classification of a structure image even under the following conditions. For example, even when the roughness of the polishing material in the final polishing in the polishing step is 0.05 μm to 2 μm, and the concentration of nitric acid in the etching solution in the etching step is 0.5% to 8%, the phases of the structure image can be accurately classified.

Second Example

A photographing condition determining method for a metal structure, a photographing method for a metal structure, a phase classification method for a metal structure, a photographing condition determining device for a metal structure, a photographing device for a metal structure, and a phase classification device for a metal structure according to a second example will be described with reference to FIGS. 4 and 5.

Photographing Condition Determining Device/Photographing Device

Figure 4:
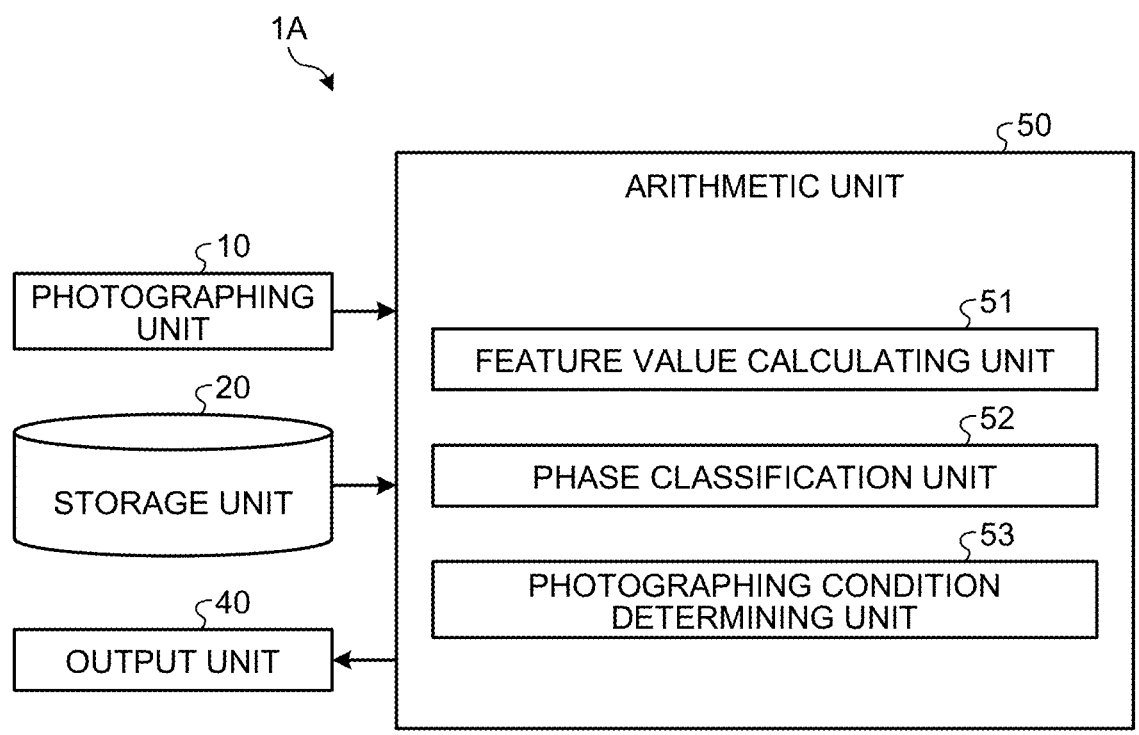
FIG. 4 is a block diagram illustrating a schematic configuration of a photographing condition determining device and a photographing device for a metal structure according to a second example.
Figure 5:
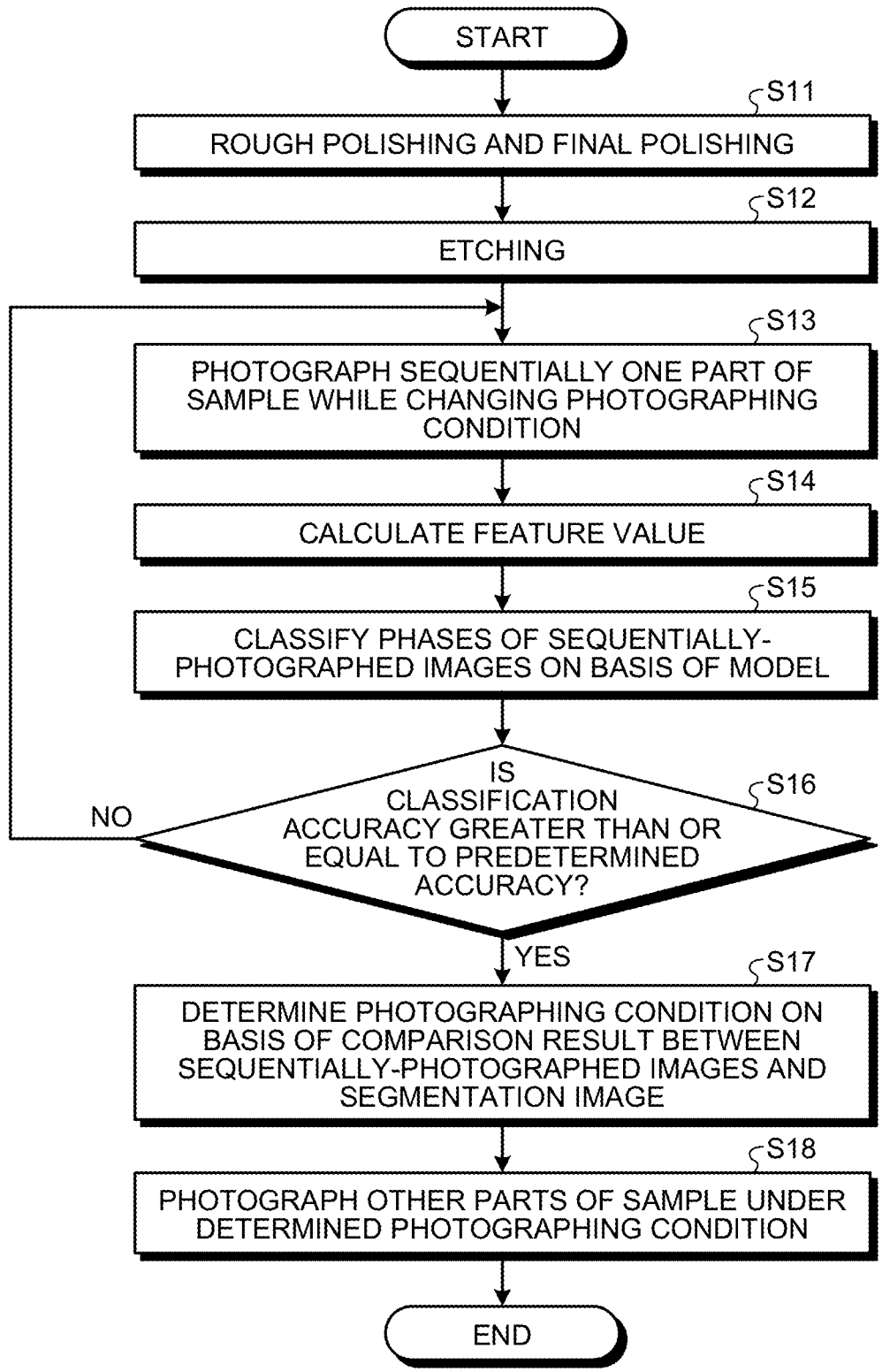
FIG. 5 is a flowchart illustrating a flow of a photographing condition determining method and a photographing method according to the second example.

As illustrated in FIG. 4, a photographing condition determining device 1A includes a photographing unit 10, a storage unit 20, an arithmetic unit 50, and an output unit 40. The photographing device according to this example is implemented by the same configuration as that of the photographing condition determining device 1A illustrated in the drawing.

Since the photographing unit 10, the storage unit 20, and the output unit 40 are the same as the photographing unit 10, the storage unit 20, and the output unit 40 of the photographing condition determining device 1 according to the first example described above, the description thereof will be omitted. The arithmetic unit 50 functions as a feature value calculating unit 51, a phase classification unit 52, and a photographing condition determining unit 53 through execution of a program. Note that details of each unit will be described later.

Photographing Condition Determining Method/Photographing Method

The photographing condition determining method using the photographing condition determining device 1A and a photographing method using the photographing device will be described with reference to FIG. 5. In the photographing condition determining method, a polishing step S11, an etching step S12, a first photographing step S13, a feature value calculating step S14, a phase classification step S15, a classification accuracy determining step S16, and a photographing condition determining step S17 are performed in the order mentioned. In the photographing method, a second photographing step S18 is performed after the steps of the photographing condition determining method.

The polishing step S11, the etching step S12, the feature value calculating step S14, the phase classification step S15, and the second photographing step S18 are similar to the polishing step S1, the etching step S2, the feature value calculating step S5, the phase classification step S6, and the second photographing step S8 of the first example. Therefore, description will be omitted. Likewise, a model used in the phase classification step S15 is also similar to the model used in the phase classification step S6 of the first example described above.

In the etching step S12, it is preferable that the etching is performed under the condition that the difference in nitric acid concentration from an etching solution in the etching step when a model has been generated is less than 0.1% and that the difference in immersion time is less than 2.0 s. As a result, the classification accuracy in the second photographing step S18 can be improved (the classification error can be reduced). Furthermore, by performing etching under the above conditions, the range of the change in the photographing condition (for example, the contrast value) in the first photographing step S13 can be reduced, and thus the number of images to be consecutively photographed can be reduced.

First Photographing Step S13

In the first photographing step S13, the photographing unit 10 consecutively photographs a part of the metal structure (a field of view of a part of the metal structure) of the metal material having been subjected to predetermined sample preparation (the polishing step S11 and the etching step S12) while changing photographing conditions. That is, in the first photographing step S13, the above-described "photographing condition" includes the contrast value and the brightness value when the photographing unit 10 is a scanning electron microscope. In addition, when the photographing unit 10 is an optical microscope, the above-described "photographing condition" includes the intensity of a light source.

In the first photographing step S13, when the photographing unit 10 is a scanning electron microscope, an acceleration voltage of 0.5 kV to 20 kV is used. Then, based on the contrast value and the brightness value initially set by the photographer, five or more images are automatically consecutively photographed while the contrast value and the brightness value are varied up and down. Furthermore, when the photographing unit 10 is an optical microscope, five or more images are automatically consecutively photographed while the intensity of the light source is varied up and down from the intensity of the light source initially set by the photographer. As the light source of the optical microscope, for example, a reflecting mirror, a tungsten lamp, or a halogen lamp can be used. In the first photographing step S13, it is desirable to photograph as many structure images as possible to improve the phase classification accuracy (reduce classification errors) in the phase classification step S15 to be described later. However, if the number of photographed images is too large, a large amount of time is required for segmentation, and thus the number of photographed images is preferably twenty images or less.

Classification Accuracy Determining Step S16

In the classification accuracy determining step S16, the photographing condition determining unit 53 determines whether the classification accuracy of segmentation in the phase classification step S15 is equal to or higher than a predetermined accuracy. Then, the photographing condition determining unit 53 proceeds to the photographing condition determining step S17 if the classification accuracy is higher than or equal to the predetermined accuracy or returns to the first photographing step S13 if the classification accuracy is higher than or equal to the predetermined accuracy.

Photographing Condition Determining Step S17

In the photographing condition determining step S17, the photographing condition determining unit 53 determines the photographing condition based on the classification result of the phase classification step S15, that is, the determination result of the classification accuracy determining step S16. In the photographing condition determining step S17, the photographing condition for photographing other parts of the metal structure (the other field of view of the metal structure) that are different from the part photographed in the first photographing step S13 is determined out of the plurality of photographing conditions used in the first photographing step S13. Specifically, in the photographing condition determining step S17, a photographing condition under which the classification accuracy of each of the phases in the phase classification step S15 is the highest among the photographing conditions used in the first photographing step S13 is determined as the photographing condition for photographing other parts of the metal structure.

After the feature value calculating step S14 is performed, the calculation result of the feature values may be output from the output unit 40. The output format at that point is not particularly limited, and the output may be performed in either format of a text file (for example, a set of numerical values) or an image file (for example, a histogram image or a structure image indicating feature values). Alternatively, the classification result of the phases may be output from the output unit 40 after the phase classification step S15 is performed. The output format at that point is not particularly limited, and the output may be performed in any format of a text file or an image file (for example, a phase classification image). In addition, the phase classification image may be output from the output unit 40 in superposition with the structure image photographed in the first photographing step S13 or next to the structure image.

In addition, in the photographing condition determining step S17, the photographing condition may be determined by receiving input from the photographing condition determining device 1A or a photographer who handles the photographing device. In this example, the photographing condition determining unit 53 outputs a plurality of structure images, of which phases have been classified, from the output unit 40 in superimposition with the respective structure images photographed in the first photographing step S13 or next to the respective structure images. Based on the output result, the photographer selects, via an input unit (not illustrated), a structure image (structure image after phase classification) in which the classification accuracy of the phases is considered to be the highest. In response to this, the photographing condition determining unit 53 determines the photographing condition corresponding to the structure image selected by the photographer as the photographing condition for photographing other parts of the metal structure.

Phase Classification Method

In the phase classification method for a metal structure according to this example, the metal structure is photographed by the photographing method described above, and metal structure phases of the metal structure are classified. The phase classification device that executes the phase classification method may be implemented by the same configuration as that of the photographing condition determining device 1 or may be implemented by a configuration different from that of the photographing condition determining device 1.

According to the photographing condition determining method for a metal structure, the photographing method for a metal structure, the phase classification method for a metal structure, the photographing condition determining device 1A for a metal structure, the photographing device for a metal structure, and the phase classification device for a metal structure as described above, the following effects are achieved. That is, in segmentation for classifying important phases of a metal structure that greatly affect various material properties such as the mechanical property or the corrosion property, the phases of the metal structure can be accurately classified even when the photographing condition varies depending on the etching condition, the photographing means, or the photographer. It is also possible to determine photographing conditions under which quantitative evaluation can be performed.

In the photographing condition determining method for a metal structure, the photographing method for a metal structure, the phase classification method for a metal structure, the photographing condition determining device 1A for a metal structure, the photographing device for a metal structure, and the phase classification device for a metal structure, the following processing is performed. First, when the structure image of the metal material after the sample preparation is photographed, photographing is consecutively performed while photographing conditions (for example, the contrast value) are varied, and a photographing condition under which classification can be accurately performed is selected based on the model prepared in advance from a plurality of photographed structure images. Then, by photographing the remaining metal material under the photographing conditions adjusted as described above, it becomes possible to cope with a difference in contrast value that fluctuates due to a slight change in etching conditions.

In addition, according to the photographing condition determining method for a metal structure, the photographing method for a metal structure, the phase classification method for a metal structure, the photographing condition determining device 1A for a metal structure, the photographing device for a metal structure, and the phase classification device for a metal structure according to this example, segmentation can be accurately performed even when the photographer or the photographing means is different. For example, in the conventional method, at the time of observing an observation sample, segmentation cannot be performed with high accuracy unless polishing and etching are performed under the same conditions as those at the time when the model has been generated. On the other hand, by using our methods, segmentation can be accurately performed even when the polishing or etching conditions at the time of model generation are not followed. As a result, it is not necessary to reproduce the polishing and etching conditions that are difficult to control, and it is possible to efficiently classify a structure image.

Material Property Estimating Device for Metal Material

The material property estimating device for a metal material ("material property estimating device") 3 will be described with reference to FIG. 6. A material property estimating device 3 includes an input unit 70, an output unit 80, an arithmetic unit 90, and a storage unit 100.

The input unit 70 is an input means that inputs an image, in which phases of a metal structure are classified ("classification image"), to the arithmetic unit 90. The classification image is an image in which the phases of the metal structure are classified by the phase classification method for a metal structure described above, an image in which the phases of the metal structure are classified by other methods such as binarization of the luminance value, or the like.

The output unit 80 is an output means that outputs an arithmetic result by the arithmetic unit 90. The output unit 80 includes, for example, a display, a printer, a smartphone or the like. The output unit 80 outputs, for example, a quantitative evaluation value of the metal structure calculated by a quantitative evaluation unit 91, data recorded in a database of the storage unit 100, an estimation result (material properties of the metal material) by a material property estimating unit 95, and the like. An output format by the output unit 80 is not particularly limited and may be, for example, data such as a text file or an image file, or the output may be in a mode of projection to an output device.

Similarly to the arithmetic units 30 and 60, the arithmetic unit 90 is implemented by, for example, a processor including a CPU or the like and a memory including a RAM, a ROM or the like. The arithmetic unit 90 implements a function matching a predetermined purpose by loading a program into a work area of the main storage unit and executing the program and controlling each component or the like through the execution of the program. In addition, the arithmetic unit 90 functions as the quantitative evaluation unit 91, a data recording unit 92, a data selection unit 93, a model generation unit 94, or a material property estimating unit 95 through the execution of the program described above. Details of each unit will be described later (see FIG. 7).

Similarly to the storage unit 20, the storage unit 100 includes a recording medium such as an EPROM, a solid state drive, and a removable medium. The storage unit 100 stores, for example, a database in which predetermined data is recorded, an estimation model (learned model) generated by the model generation unit 94, and the like. In the above-described database, for example, quantitative evaluation values of a metal structure calculated by the quantitative evaluation unit 91, material property values (steel plate data) of a metal material obtained in advance by a mechanical test or the like, the component composition of a metal material, a metal material and the like are recorded.

Material Property Estimating Method for Metal Material

Figure 7:
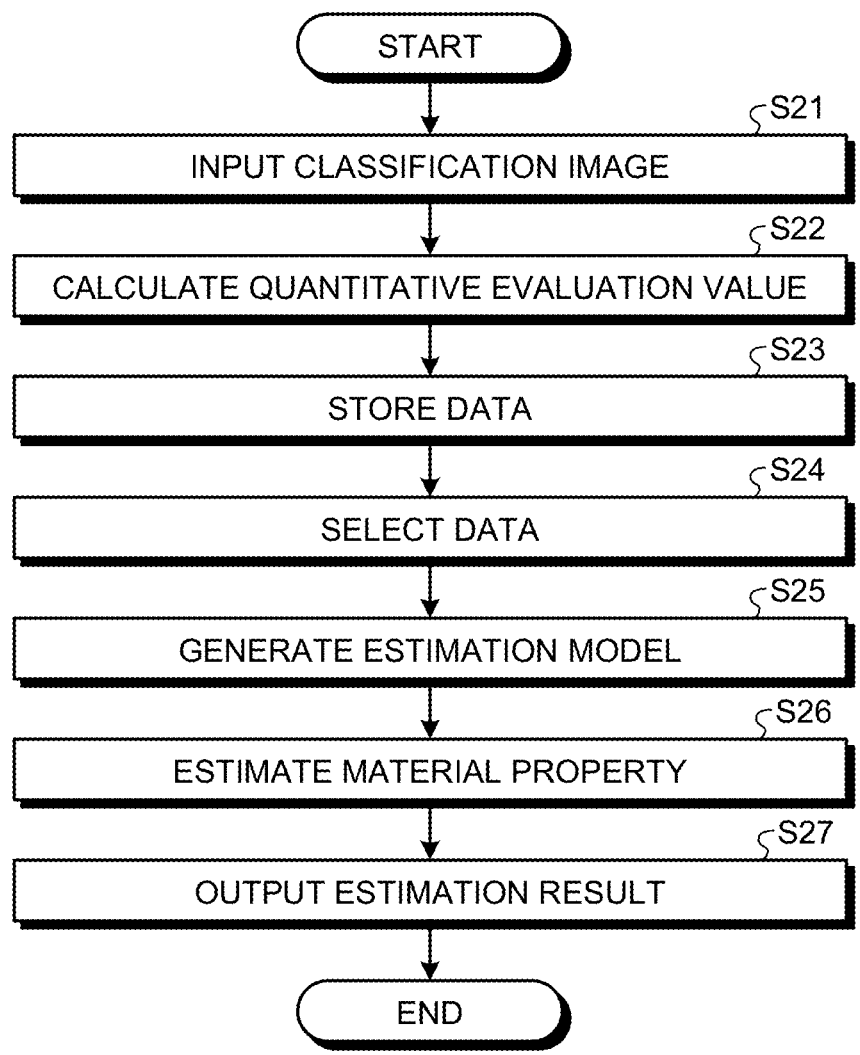
FIG. 7 is a flowchart illustrating a flow of a material property estimating method for a metal material according to an example.

A phase learning method for a metal structure using the material property estimating device 3 will be described with reference to FIG. 7. The phase learning method for a metal structure is performed after performing the phase classification method for a metal structure described above by using the classification result (classification image). In the phase learning method for a metal structure, an image input step S21, a quantitative evaluation step S22, a data recording step S23, a data selection step S24, a model generating step S25, a material property estimating step S26, and an estimation result output step S27 are performed in the order mentioned.

Image Input Step S21

In the image input step S21, the input unit 70 inputs the classification image to the arithmetic unit 90.

Quantitative Evaluation Step S22

In the quantitative evaluation step S22, the quantitative evaluation unit 91 calculates quantitative evaluation values of the metal structure by quantitatively evaluating each of phases included in the classification image. In the quantitative evaluation step S22, for example, quantitative evaluation values as described in (1) to (5) are calculated.

(1) Area Ratio

An area ratio of a phase is calculated by deriving the areas of the classified phases.

(2) Major Axis, Minor Axis, Aspect Ratio

The major axis, the minor axis, or the aspect ratio of an ellipsoid is calculated by elliptically approximating the shape of each grain of a classified phase.

(3) Feret Diameter

A straight line is drawn from an interface of each grain of a classified phase, and a Feret's diameter at which the length of the straight line is maximized is calculated.

(4) Average Diameter

The area of each grain of a classified phase is derived, and the square root of the area is derived to derive the average diameter of grains.

(5) Roundness

The area and the circumferential length of each grain of a classified phase are derived, and the roundness of the grain is calculated by Equation (4). The roundness is 1.0 when the grain is a perfect circle, and conversely, the roundness becomes smaller than 1.0 as the grain is farther from the shape of the perfect circle.

$$C = 4\pi \frac{S}{P^2} \qquad (4)$$

where, C: roundness,
S: area, and
P: circumferential length

Since the quantitative evaluation values (2) to (5) are calculated for each grain, a plurality of numerical values can be obtained even for one structure image, and a histogram of each of the quantitative evaluation values can be created.

Data Recording Step S23

In the data recording step S23, the data recording unit 92 records the quantitative evaluation values of the metal structure calculated in the quantitative evaluation step S22 in the database of the storage unit 100.

Data Selection Step S24

In the data selection step S24, the data selection unit 93 selects (extracts) data to be used for estimation of material properties of the metal material from the quantitative evaluation values of the metal structure and data of the material properties of the metal material recorded in the database.

Since the quantitative evaluation value is calculated for each grain, a plurality of numerical values may be obtained for one structure image. For example, since one average diameter of the quantitative evaluation values (4) is obtained for each grain, a plurality of numerical values is obtained for one image. Among the plurality of pieces of numerical information, an average value may be calculated, and only the average value may be used to estimate the material properties, or the standard deviation may be used to estimate the material properties. In addition, in the data selection step S24, it is desirable to select a quantitative evaluation value with a high accuracy of estimation of the material properties in the estimation model generating step S25 to be described later. Therefore, for example, in the material property estimating step S26 described later, when the estimation accuracy is poor, it is preferable to return to this step and to select data again. In addition to the quantitative evaluation values of the metal structure, the component composition of the metal material or a heat treatment condition may be input.

Estimation Model Generating Step S25

In the estimation model generating step S25, the model generation unit 94 generates an estimation model for estimating the material properties of the metal material using the data selected in the data selection step S24. Specifically, in the estimation model generating step S25, an estimation model for estimating the material properties is generated using the quantitative evaluation value selected in the data selection step S24, the component composition of the metal material, the heat treatment condition, and the like. At that point, the estimation model is generated using the data of the material properties of the metal material similarly selected in the data selection step S24.

The estimation model may be generated using a model such as a neural network, support vector regression, or Gaussian process regression or may be generated as a simple regression formula such as linear regression. In addition, in the generation of the estimation model, it is preferable to estimate the material properties using a plurality of estimation models and to adopt an estimation model with the highest estimation accuracy.

The estimation accuracy of the material properties is evaluated by, for example, plotting measured values on the X-axis and estimated values on the Y-axis and checking how much the two types of data match with each other by a two-dimensional graph, by a parameter obtained by adding an estimation error of each piece of data and dividing the result by the number of pieces of data, or by others. In addition, the estimation accuracy of the material properties is preferably evaluated by, for example, the following procedure. First, the data selected from the database is divided into data used for parameter fitting in the estimation model (training data) and data not used for fitting (test data). Then, the estimation accuracy of the material properties is evaluated based on the degree of coincidence between the estimated values and the measured values of the test data. When the data selected from the database is divided into the training data and the test data, the data may be selected and divided by the worker or may be randomly determined using random numbers or the like after the ratios of the training data and the test data are determined.

Material Property Estimating Step S26

In the material property estimating step S26, the material property estimating unit 95 estimates the material properties of the metal material using the estimation model generated in the estimation model generating step S25. Specifically, in the material property estimating step S26, the quantitative evaluation values selected in the data selection step S24 are input to the estimation model generated in the estimation model generating step S25, thereby estimating the material properties of the metal material.

Estimation Result Output Step S27

In the estimation result output step S27, the output unit 80 outputs the estimation result in the material property estimating step S26, that is, the material properties of the metal material.

Meanwhile, in the conventional method, it is difficult to efficiently classify phases of a metal structure and to quantitatively evaluate a metal structure using an image in which the phases are classified, and thus it is difficult to accurately estimate the material properties from the structure image. On the other hand, according to the material property estimating method for a metal material and the material property estimating device for a metal material, quantitative evaluation can be efficiently performed from the classification result of phases of the metal structure. Therefore, by deriving a correlation between the quantitative evaluation value and the material properties of the metal material, the material properties of the metal material can be accurately estimated. As a result, the material properties of the metal material can be grasped at the same time as the image of the metal structure is viewed, and thus the efficiency of development of a metal material (for example, a steel plate) can be improved.

In addition, according to the material property estimating method for a metal material and the material property estimating device for a metal material according to this example, the quantitative evaluation of a metal structure can be efficiently performed by efficient segmentation of the structure image unlike in the prior art. In addition, by using an index quantified in this manner, it is possible to accurately estimate the material properties of a photographed structure image.

EXAMPLES

First Example

Examples of the photographing condition determining method and the photographing method according to the first example will be described with reference to FIGS. 8 to 12. In this example, first, to configure a database of feature values of the ferrite phase and the martensite phase, a DP steel plate ("sample") was roughly polished, and then final polishing was performed using 0.06 μm alumina as a polishing agent until no flaws were observed when observed with an optical microscope with a magnification of 500 times (polishing step). Subsequently, the sample after the final polishing was rubbed with gauze impregnated with a nital solution having a nitric acid concentration of 1% for 3 seconds and then rinsed with distilled water, thereby performing etching (etching step). Subsequently, the structure image of the etched sample was photographed using a scanning electron microscope (photographing step).

Figure 8:
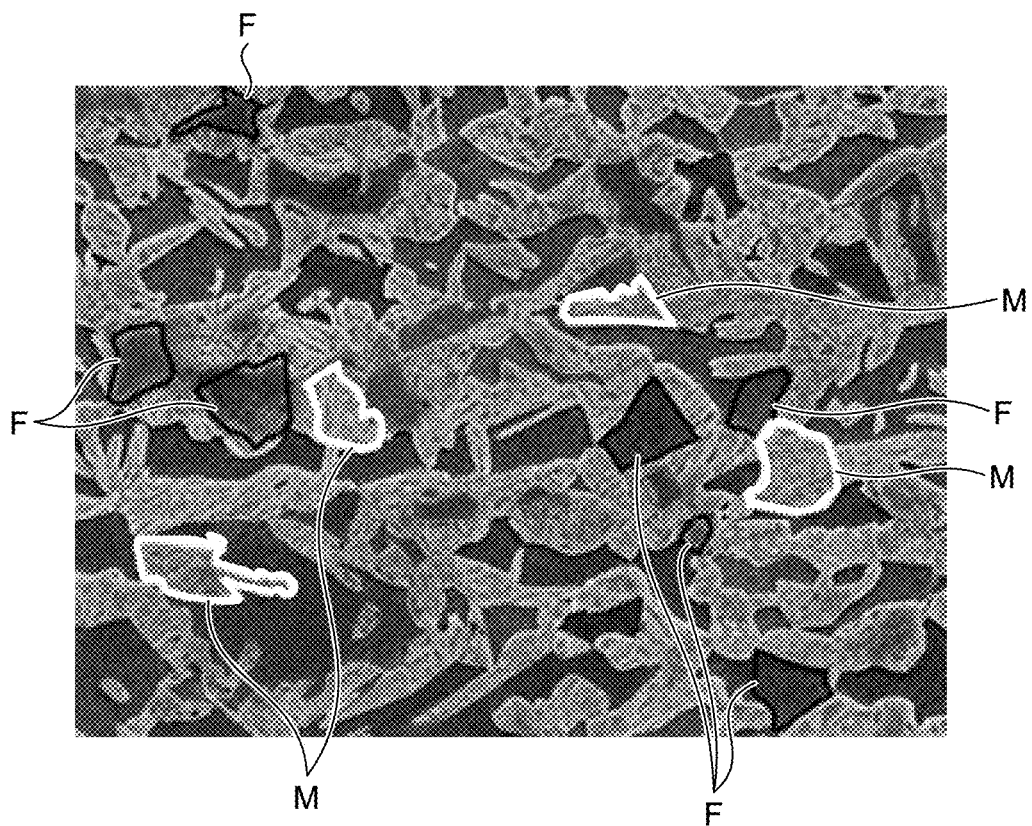
FIG. 8 is a diagram illustrating an example of a photographing condition determining method and a photographing method according to the first example and illustrating phases of a metal structure specified when a database is configured.
Figure 9A:
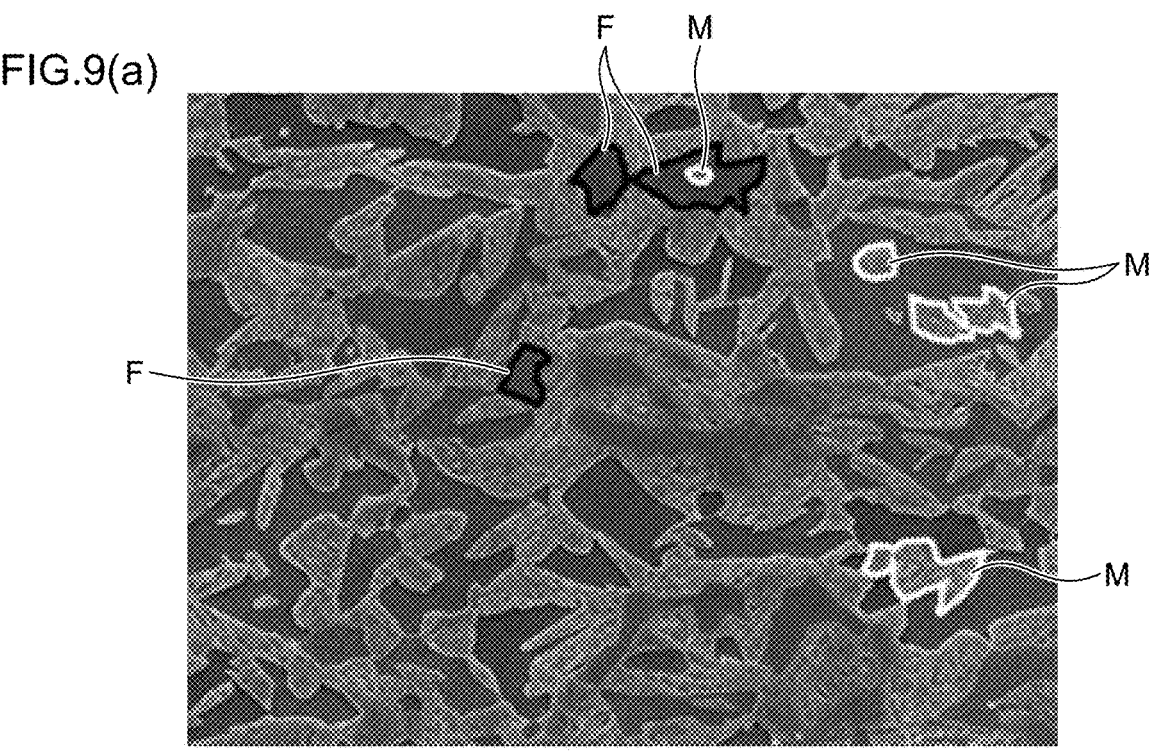
FIG. 9 is a diagram illustrating (FIG. 9(a)) an example of the photographing condition determining method and the photographing method according to the first example and illustrating (FIG. 9(b)) phases of a metal structure specified in a phase specification step.
Figure 9B:
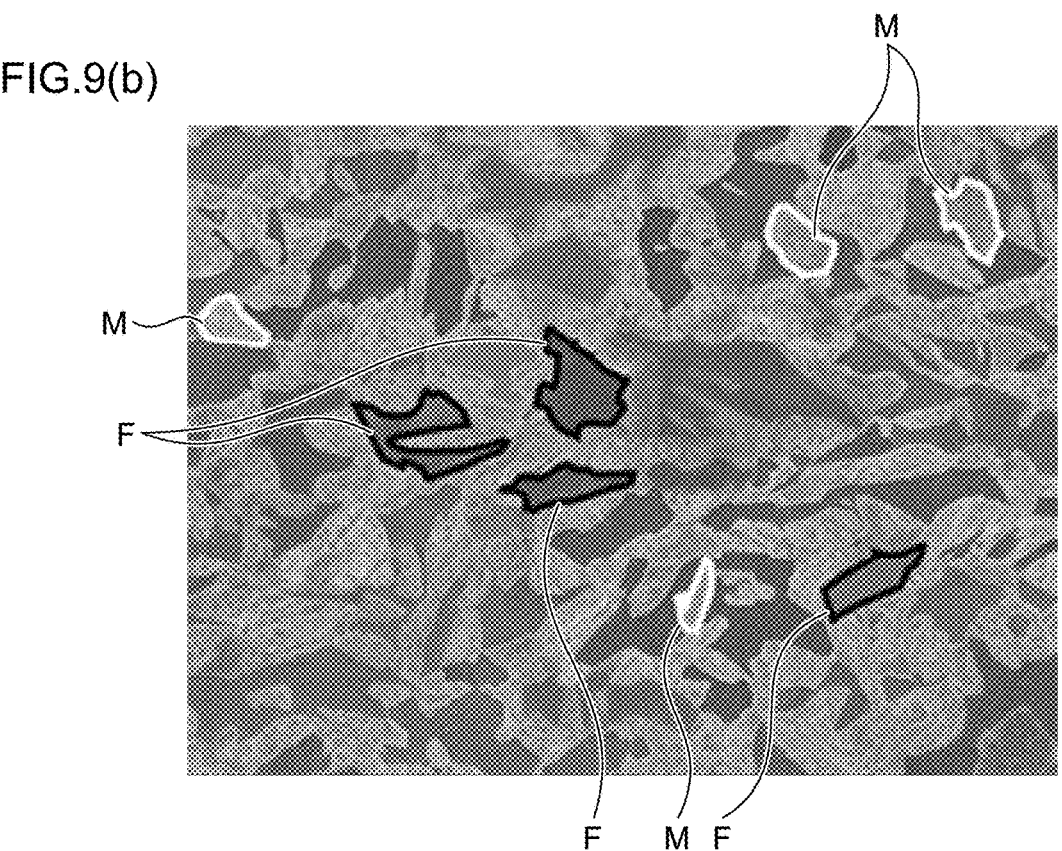
Figure 10A:
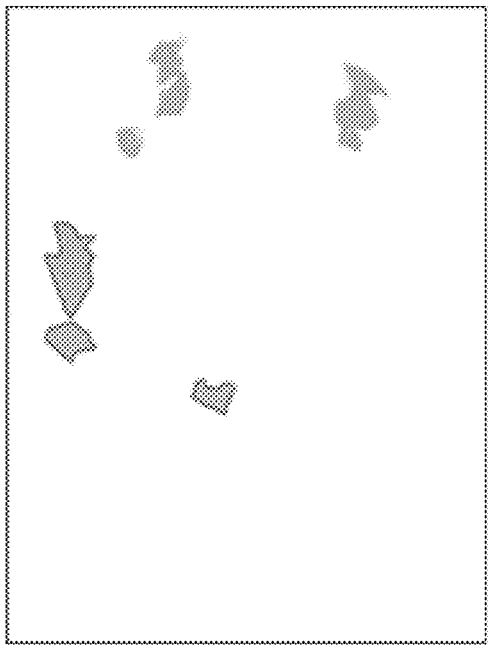
FIGS. 10(a)-10(d) are diagrams illustrating an example of the photographing condition determining method and the photographing method according to the first example and illustrating results of classification in a phase classification step. In (b) and (d) of FIG. 10, regions that have been correctly classified are indicated in gray.
Figure 10B:
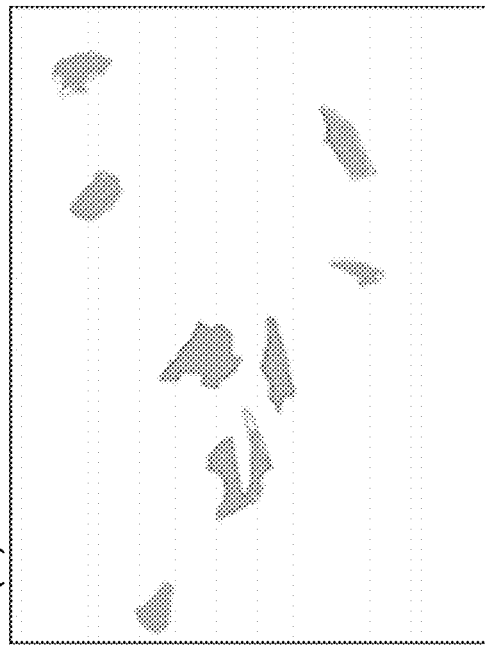
Figure 10C:
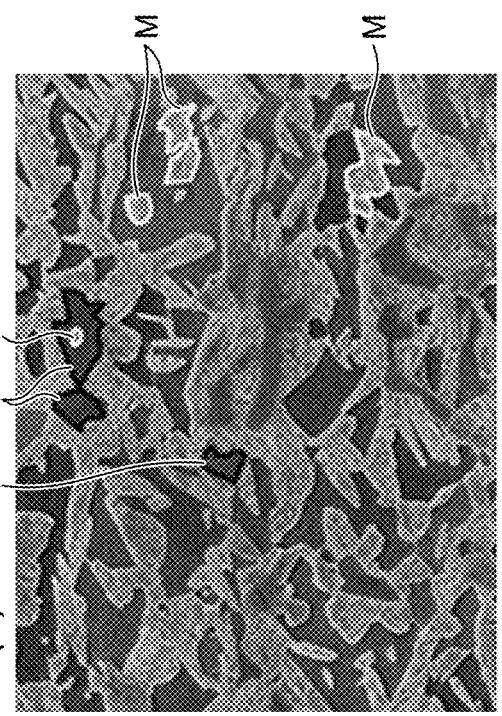
Figure 10D:
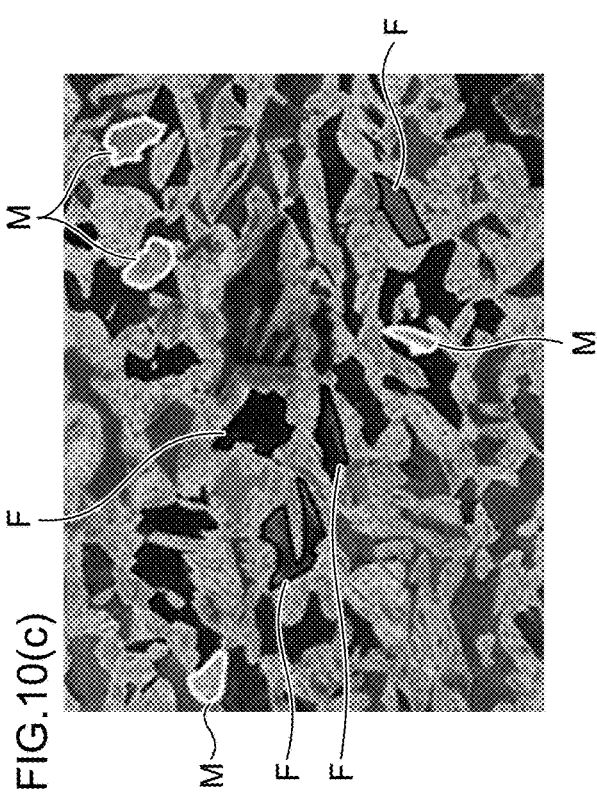

Subsequently, as illustrated in FIG. 8, the ferrite phase and the martensite phase were specified in the structure image (phase specification step). Subsequently, for the two specified phases, the identical feature value, the Mean feature value of 2 pixels to 32 pixels, the Gaussian feature value, the Median feature value, the Max feature value, the Min feature value, the Derivative feature value, and the Derivative addition feature value were calculated, and a database of the feature values for each of the phases was configured (feature value calculating step). Subsequently, binarization was repeatedly performed so that the previously specified ferrite phase and the martensite phase were classified with an accuracy higher than or equal to 95%, thereby creating a decision tree for classifying the ferrite phase and the martensite phase (model generating step).

Subsequently, a sample different from the sample used when the database had been configured was roughly polished, and then final polishing and etching were performed by two methods (method A and method B) different from the method used when the database had been configured as illustrated in the following Table 1 (polishing step and etching step). Subsequently, structure images of a part of the two etched samples were photographed at a plurality of contrast values using a scanning electron microscope (first photographing step). Subsequently, as illustrated in (a) and (b) of FIG. 9, a plurality of ferrite phases and a plurality of martensite phases were specified in structure images of two types of samples that had been photographed (phase specification step). Subsequently, feature values similar to those at the time of configuring the database were calculated for the specified regions (feature value calculating step), and phases were classified based on the decision tree (phase classification step).

TABLE 1

| | Final Polishing | Etching |
|---|---|---|
| Method A | Polishing agent: 0.06 μm alumina<br>Polishing method: polish until no flaws are observed when observed with optical microscope with magnification of 500 times. | Etching solution: 1% nital<br>Etching method: rub sample with gauze impregnated with nital for 5 s and then rinse with distilled water. |
| Method B | Polishing agent: 0.5 μm diamond<br>Polishing method: polish until no flaws are observed when observed with optical microscope with magnification of 1000 times. | Etching solution: 5% nital<br>Etching method: immerse sample for 5 s and then rinse with distilled water |

Subsequently, as illustrated in (a) to (d) of FIG. 10, among the contrast values at the time of photographing, a contrast value with which classification can be most accurately performed was determined (photographing condition determining step). In (b) of FIG. 10, a region correctly classified in (a) is indicated in gray. Meanwhile, in (d) of FIG. 10, a region correctly classified in (c) is illustrated in gray. Subsequently, structure images of other parts of the two samples were photographed under the determined contrast value (second photographing step).

Figure 11A:
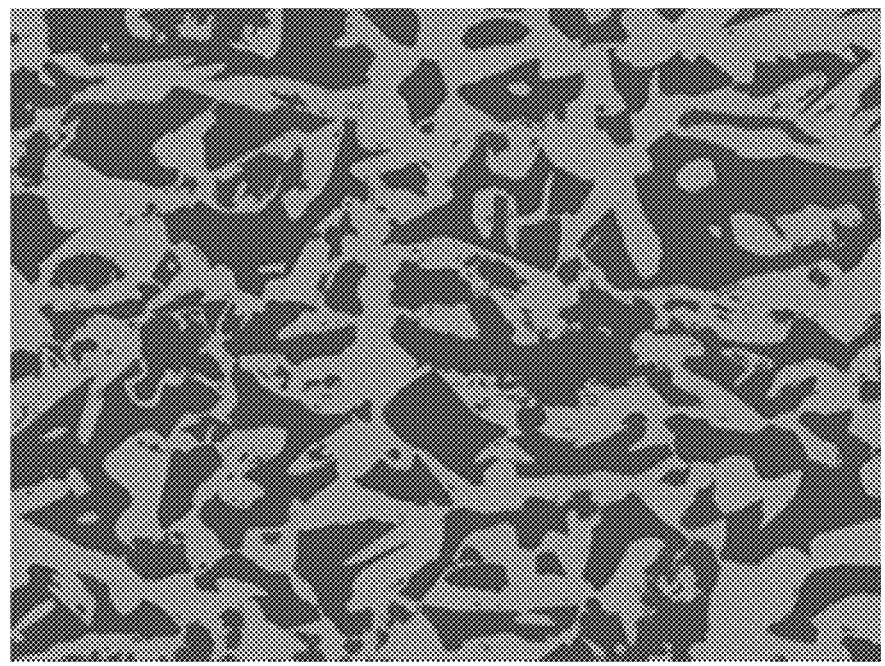
FIG. 11 is a diagram illustrating (FIG. 11(a)) an example of the photographing condition determining method and the photographing method according to the first example and illustrating (FIG. 11(b)) phases of a metal structure classified in the phase classification step for a structure image photographed by adjusting a contrast value in a second photographing step.
Figure 11B:
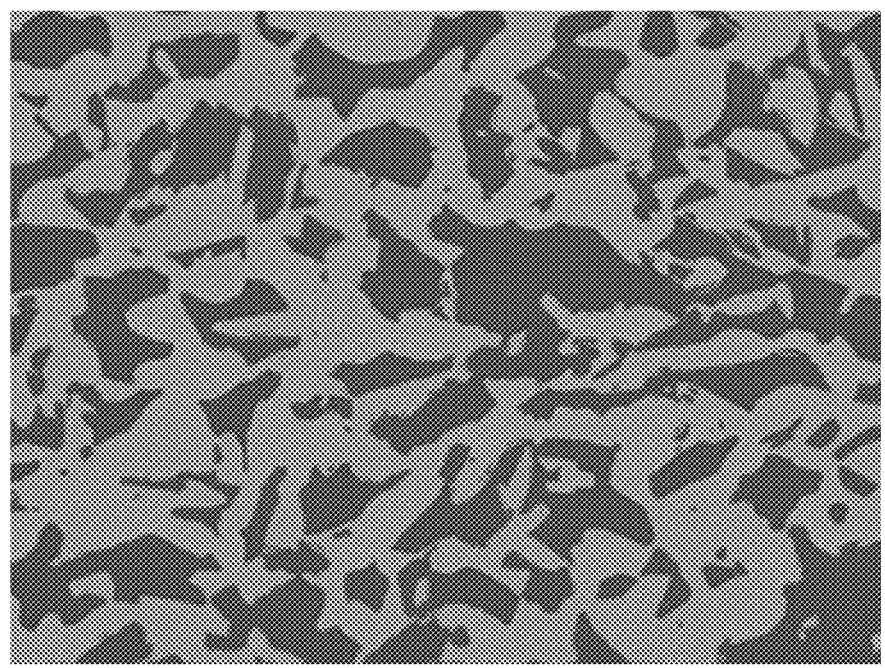
Figure 12A:
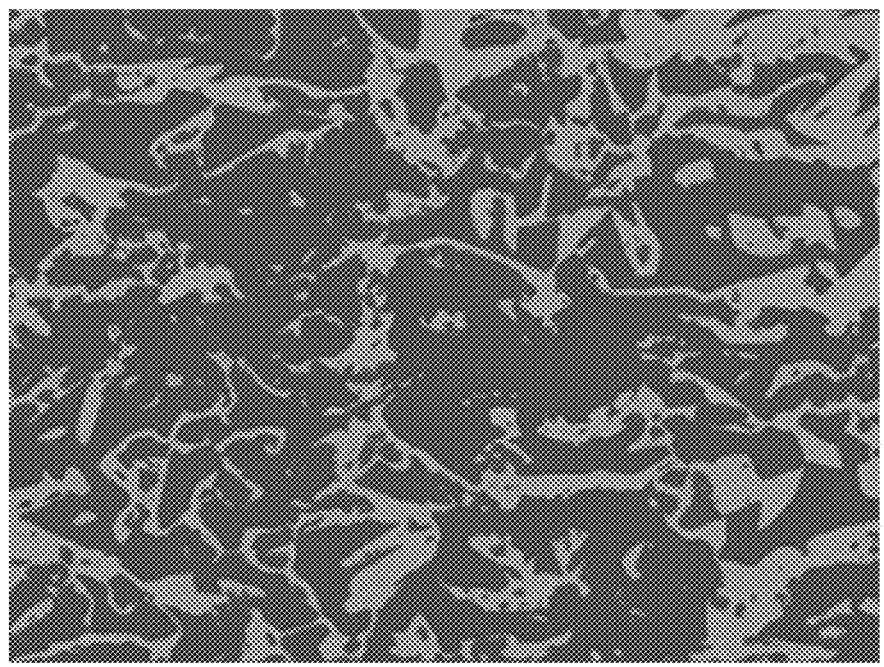
FIG. 12 is a diagram illustrating (FIG. 12(a)) an example of the photographing condition determining method and the photographing method according to the first example and illustrating (FIG. 12(b)) phases of a metal structure classified in the phase classification step for a structure image photographed without adjusting a contrast value.
Figure 12B:
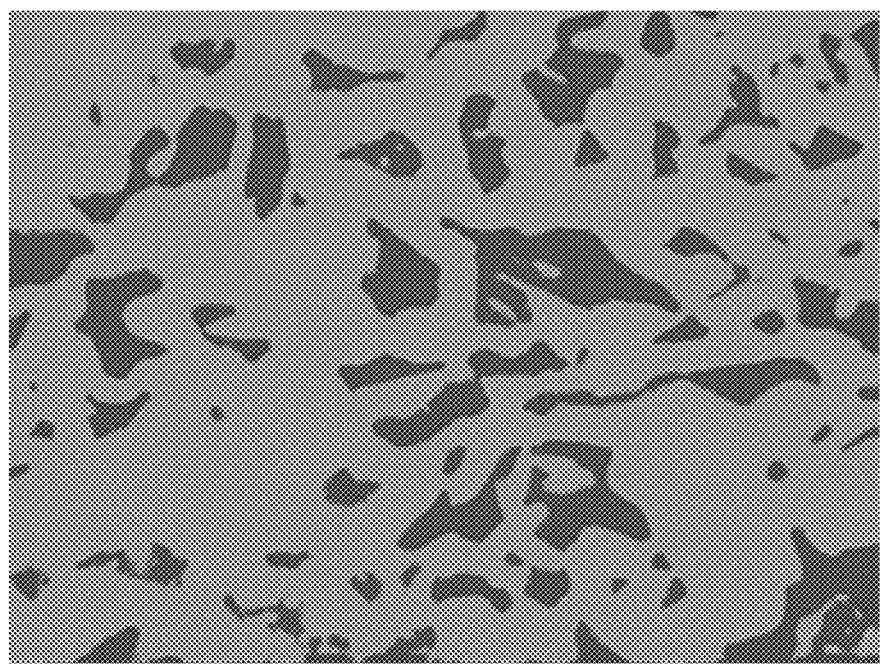
Figure 15A:
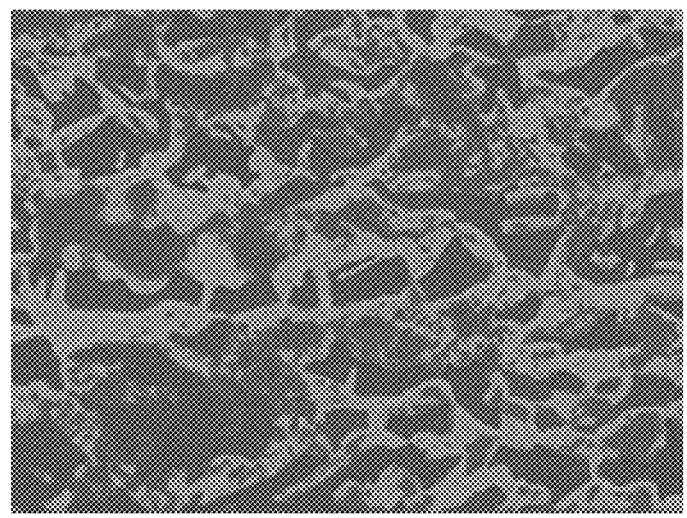
FIG. 15 is a diagram illustrating (FIG. 15(a)) a comparative example of the photographing condition determining method and the photographing method according to the second example and illustrating (FIG. 15(b)) structure images photographed without changing the contrast value and phase classification images corresponding to the structure images.
Figure 15B:
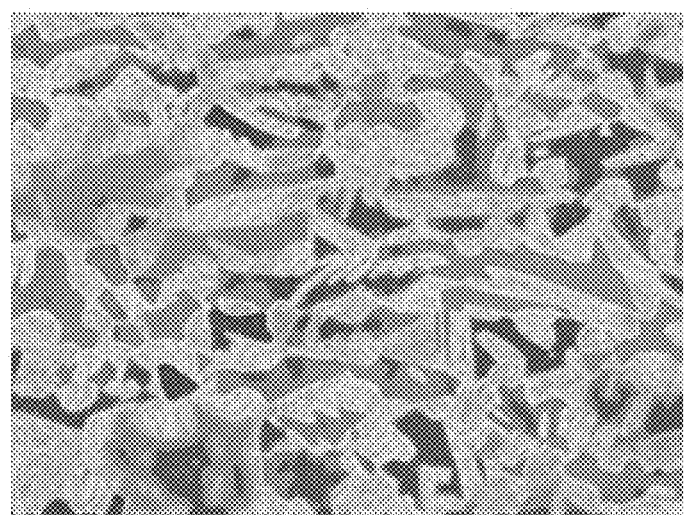

A result of segmentation performed on a structure image of a sample prepared by the method A of Table 1 is illustrated in (a) of FIG. 11, and a result of segmentation performed on a structure image of a sample prepared by the method B is illustrated in (b) of FIG. 11. For comparison, segmentation results of structure images of the samples prepared by the methods A and B in Table 1 without performing the contrast adjustment according to our method are further illustrated in (a) and (b) of FIG. 12, respectively.

As illustrated in (a) and (b) of FIG. 11, it can be seen that classification can be performed accurately by performing contrast adjustment by our method. On the other hand, as illustrated in (a) and (b) of FIG. 12, it can be seen that the classification cannot be performed accurately when the contrast adjustment by our method is not performed.

As described above, by using our method, it is possible to obtain a contrast value with high classification accuracy at the time of segmentation even for a sample adjusted under an etching condition different from that at the time of configuring the database, and thus, it is possible to perform segmentation accurately.

Second Example

Examples of the photographing condition determining method and the photographing method according to the second example will be described with reference to FIGS. 8 and 13 to 15. In this example, first, to configure a database of feature values of the ferrite phase and the martensite phase, a DP steel plate ("sample") was roughly polished, and then final polishing was performed using 0.06 μm alumina as a polishing agent until no flaws were observed when observed with an optical microscope with a magnification of 500 times (polishing step). Subsequently, the sample after the final polishing was rubbed with gauze impregnated with a nital solution having a nitric acid concentration of 1% for 3 seconds and then rinsed with distilled water, thereby performing etching (etching step). Subsequently, the structure image of the etched sample was photographed using a scanning electron microscope (photographing step).

Subsequently, as illustrated in FIG. 8, the ferrite phase and the martensite phase were specified in the structure image (phase specification step). Subsequently, for the two specified phases, the identical feature value, the Mean feature value of 2 pixels to 32 pixels, the Gaussian feature value, the Median feature value, the Max feature value, the Min feature value, the Derivative feature value, and the Derivative addition feature value were calculated, and a database of the feature values for each of the phases was configured (feature value calculating step). Subsequently, binarization was repeatedly performed so that the previously specified ferrite phase and the martensite phase were classified with an accuracy higher than or equal to 95%, thereby creating a decision tree for classifying the ferrite phase and the martensite phase (model generating step).

Subsequently, a sample different from the sample used when the database had been configured was roughly polished, and then final polishing and etching were performed by two methods (method A and method B) different from a method used when the database had been configured as illustrated in the Table 1 (polishing step and etching step). Subsequently, using a scanning electron microscope, five structure images of a part of the two samples after the etching were consecutively photographed while the contrast value was automatically and consecutively varied at an acceleration voltage of 15 kV (first photographing step). Then, feature values similar to those at the time of configuring the database were calculated for the structure images of two types x five images (feature value calculating step), and phases were classified based on the decision tree (phase classification step).

A result of segmentation performed on a structure image of a sample prepared by the method A of Table 1 is illustrated in FIG. 13, and a result of segmentation performed on a structure image of a sample prepared by the method B is illustrated in FIG. 14. For comparison, a result obtained by photographing only one image without photographing consecutively in the first photographing step and performing segmentation is illustrated in (a) and (b) of FIG. 15. In FIGS. 13 and 14, a structure image photographed in the first photographing step, a phase classification image indicating the phase classification result in the phase classification step, and whether the classification accuracy is good or not are illustrated in order from the left.

In the segmentation result of FIG. 13, the phase classification accuracy is the best in the example of (e). Therefore, it is understood that other parts of the metal structure are only required to be photographed in the second photographing step using the contrast value used when the structure image of (e) was photographed. Meanwhile, in the segmentation result of FIG. 14, the phase classification accuracy is the best in the example of (c). Therefore, it is understood that other parts of the metal structure are only required to be photographed in the second photographing step using the contrast value used when the structure image of (c) was photographed. On the other hand, since the phase classification accuracy is poor in the segmentation result of FIG. 15, it is expected that the phase classification accuracy will be naturally poor in photographing, in the second photographing step, using the contrast value used when the structure image in the figure has been photographed.

As described above, by using our method, it is possible to obtain a contrast value with high classification accuracy at the time of segmentation even for a sample adjusted under an etching condition different from that at the time of configuring the database, and thus, it is possible to perform segmentation accurately.

Third Example

Figure 16A:
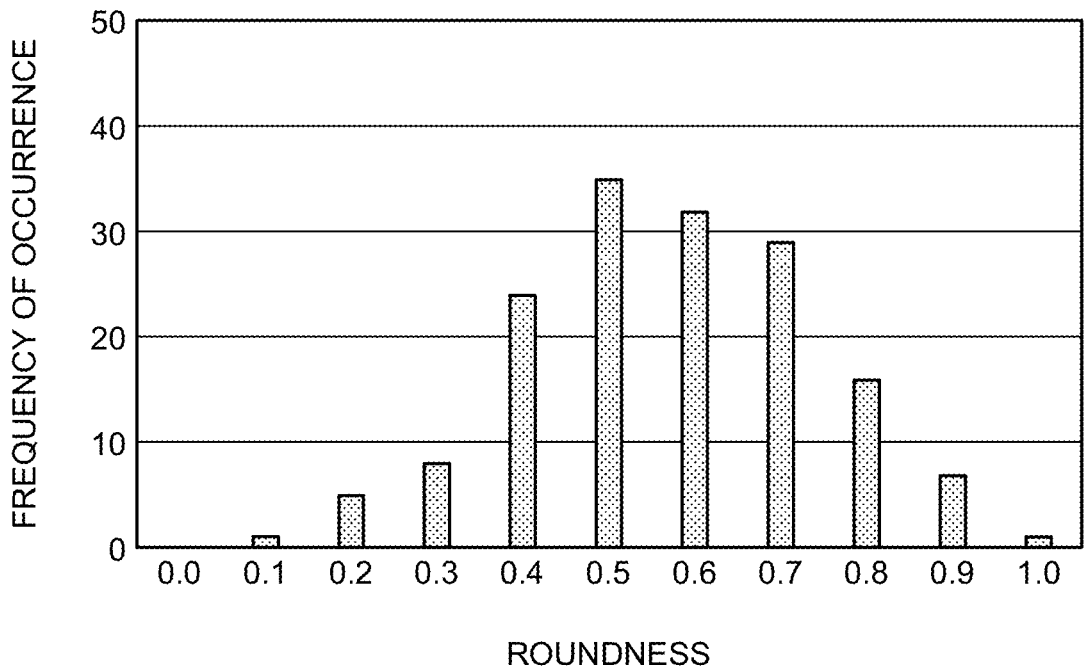
FIGS. 16(a) and 16(b) include graphs illustrating an example of a material property estimating method for a metal material and illustrating histograms of roundness of the ferrite phase and the martensite phase calculated from the structure images of (a) of FIG. 11.
Figure 16B:
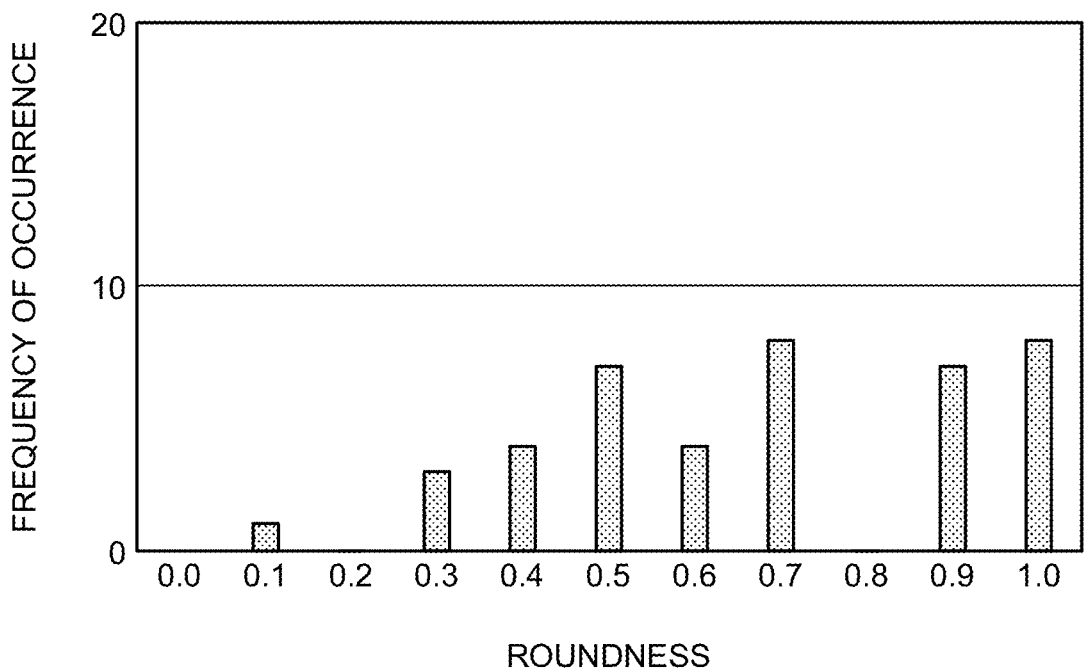
Figure 17A:
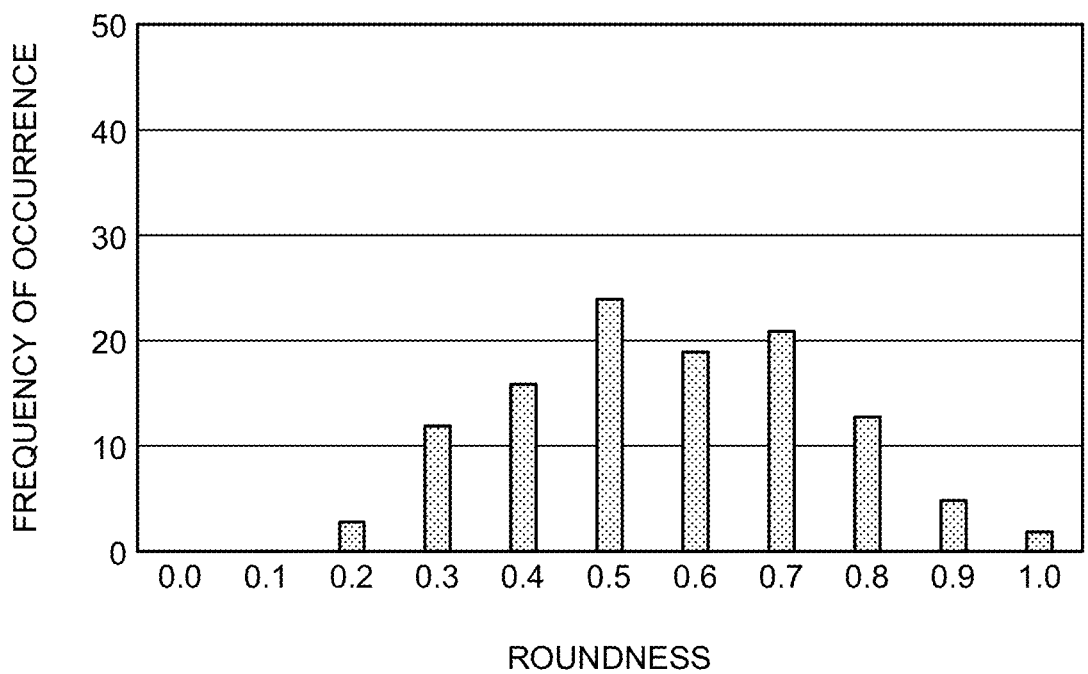
FIGS. 17(a) and 17(b) include graphs illustrating an example of a material property estimating method for a metal material and illustrating histograms of roundness of the ferrite phase and the martensite phase calculated from the structure images of (b) of FIG. 11.
Figure 17B:
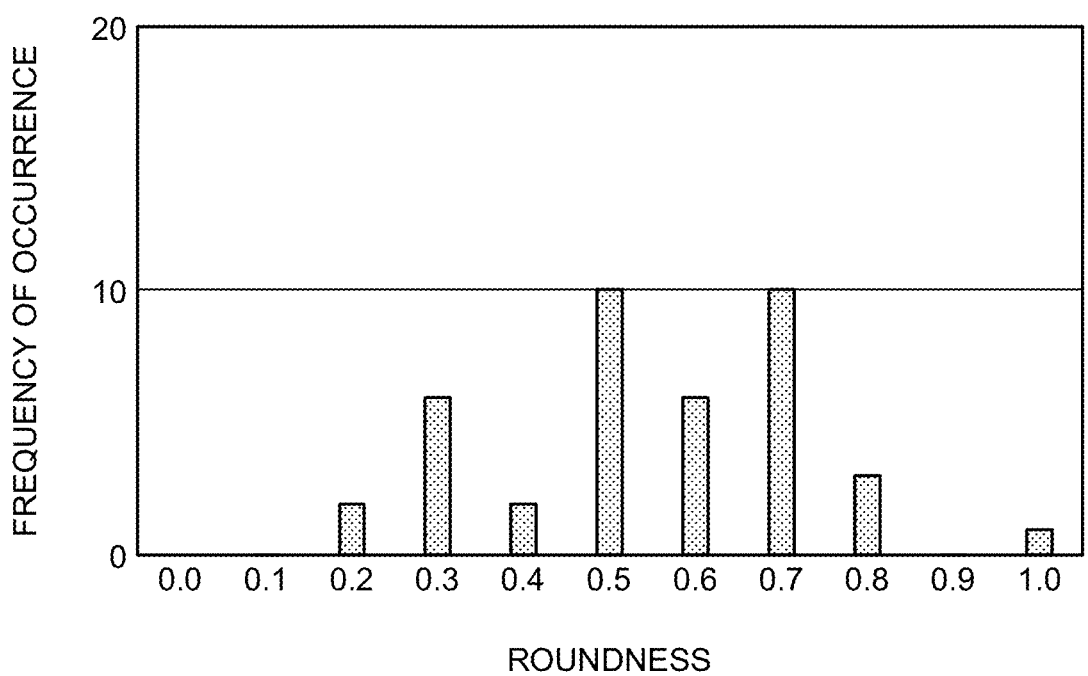

A third example of the material property estimating method for metal material and the material property estimating device for a metal material will be described with reference to FIGS. 16 to 18.

In this example, first, a quantitative evaluation of the metal structure was performed using the classification result (see (a) and (b) of FIG. 11) of the first example described above (quantitative evaluation step). At that point, histograms of the area ratio and the roundness were calculated for the ferrite phase and the martensite phase. Illustrated in (a) of FIG. 16 is a histogram of the roundness of the ferrite phase calculated from the classification result of the first example (see (a) of FIG. 11). Moreover, illustrated in (b) of FIG. 16 is a histogram of the roundness of the martensite phase calculated from the classification result of the first example (see (a) of FIG. 11). Furthermore, illustrated in (a) of FIG. 17 is a histogram of the roundness of the ferrite phase calculated from the classification result of the first example (see (b) of FIG. 11). Also, illustrated in (b) of FIG. 17 is a histogram of the roundness of the martensite phase calculated from the classification result of the first example (see (b) of FIG. 11).

Subsequently, the component composition of the metal material was selected in addition to the average values of the area ratios and the roundness of the ferrite phase and the martensite phase among the quantitative evaluation values calculated above and the quantitative evaluation values (data selection step), and these pieces of data were used for estimation of the material properties.

Subsequently, data for one hundred steel types was randomly extracted from the database of DP steel plates including structure images and component compositions and tensile strengths of metal materials. Then, these extracted pieces of data were similarly classified into phases, and then average values of the area ratios and the roundness of the ferrite phase and the martensite phase were calculated.

Subsequently, an estimation model for estimating the tensile strength was generated from the quantitative evaluation values and the component composition of the metal material (estimation model generating step). At this point, the extracted data was randomly divided into training data and test data at a ratio of 9:1. In addition, an estimation model for estimating the tensile strength was generated using a neural network model.

Subsequently, to verify the estimation accuracy of the estimation model, measured values and the estimated values of the tensile strength were compared. FIG. 18 is a diagram illustrating an estimation result of the tensile strength by a neural network model generated by the model generation unit. In the figure, the horizontal axis represents the measured value of the tensile strength normalized using the average value and the standard deviation of the tensile strength extracted from the database. The vertical axis represents the estimated value of the tensile strength normalized using the average value and the standard deviation of the tensile strength extracted from the database. Meanwhile, in the drawing, a round plot point indicates an estimation result of the tensile strength of a sample used for parameter adjustment in the neural network model (training data). A square plot point indicates an estimation result of the tensile strength of a sample that is not used for the parameter adjustment (test data).

Figure 18:
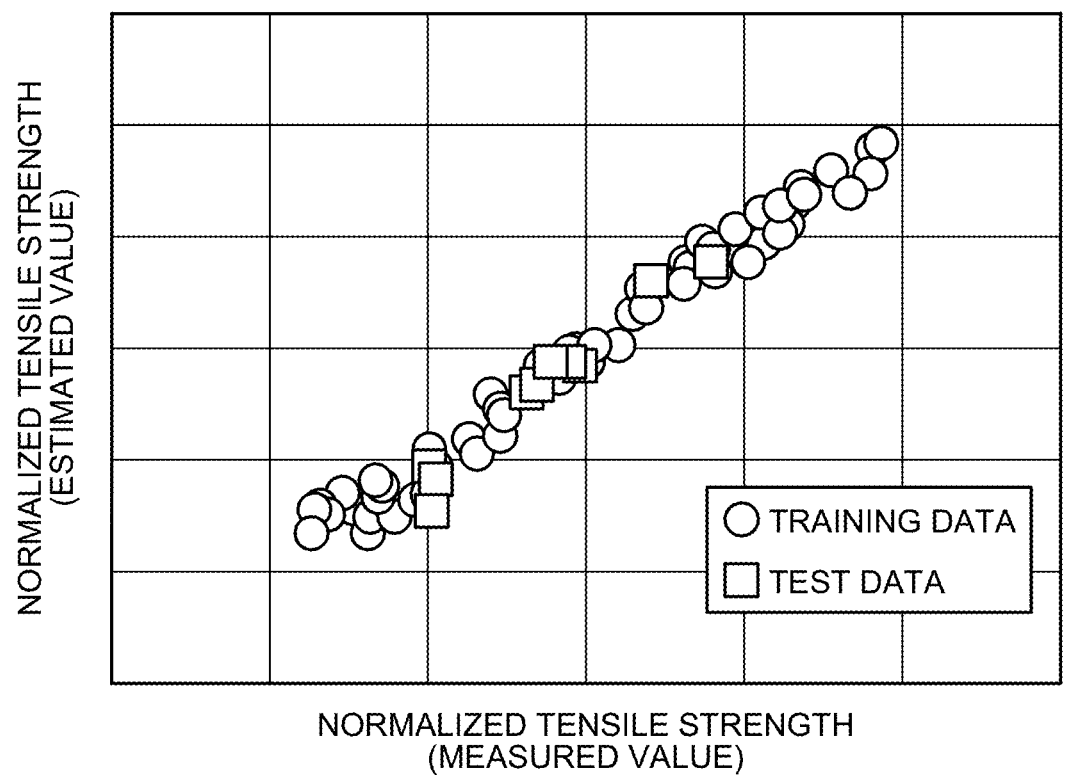
FIG. 18 is a graph illustrating an example of a material property estimating method for a metal material and illustrating estimation results of tensile strength by an estimation model (neural network model) generated by an estimation model generating unit.

As illustrated in FIG. 18, it can be seen that both the training data and the test data have good estimation accuracy of material properties and that the tensile strength can be accurately estimated by using the average values of the area ratios and the roundness of the ferrite phase and the martensite phase and the component composition of the metal material.

In addition, after configuring the estimation model, estimated values of the tensile strength corresponding to the metal structures of (a) and (b) of FIG. 11 were calculated using the calculated quantitative evaluation values and the component composition of the metal material. The quantitative evaluation values calculated from the structure images, estimated values and measured values of the tensile strength are illustrated in Table 2. As illustrated in Table 2, it can be seen that the tensile strength is accurately estimated.

TABLE 2

| Structure Image | Martensite | | Ferrite | | Normalized Tensile Strength (Estimated Value) | Normalized Tensile Strength (Measured Value) |
| --- | --- | --- | --- | --- | --- | --- |
| | Area Ratio (%) | Roundness (Average Value) | Area Ratio (%) | Roundness (Average Value) | | |
| FIG. 11 (a) | 55 | 0.522 | 45 | 0.519 | 1.13 | 1.09 |
| FIG. 11 (b) | 53 | 0.461 | 47 | 0.475 | 1.06 | 1.09 |

Although the photographing condition determining method for a metal structure, the photographing method for a metal structure, the phase classification method for a metal structure, the photographing condition determining device for a metal structure, the photographing device for a metal structure, the phase classification device for a metal structure, the material property estimating method for a metal material, and the material property estimating device for a metal material have been specifically described with reference to the examples and the examples for carrying out our methods, the spirit of this disclosure is not limited to these descriptions and should be widely interpreted based on the appended claims. Various modifications, variations and the like based on these descriptions are also included in this disclosure.

Our photographing condition determining method for a metal structure, the photographing method for a metal structure, the phase classification method for a metal structure, and the material property estimating method for a metal material may be implemented by introducing software in which the methods are implemented into a generally commercially available computer. A commercially available computer refers to, for example, an arithmetic unit including a CPU that executes a command of a program that is software for implementing each function, a recording medium (for example, a hard disk or a USB memory) on which the software and various types of data are recorded in a format readable by the computer (or the CPU), a RAM that loads the program, a GPU that is a processor specialized for image processing and the like. Furthermore, our methods may be implemented not only by a commercially available computer but also by introducing software into a cloud computer on a network.

Figure 6:
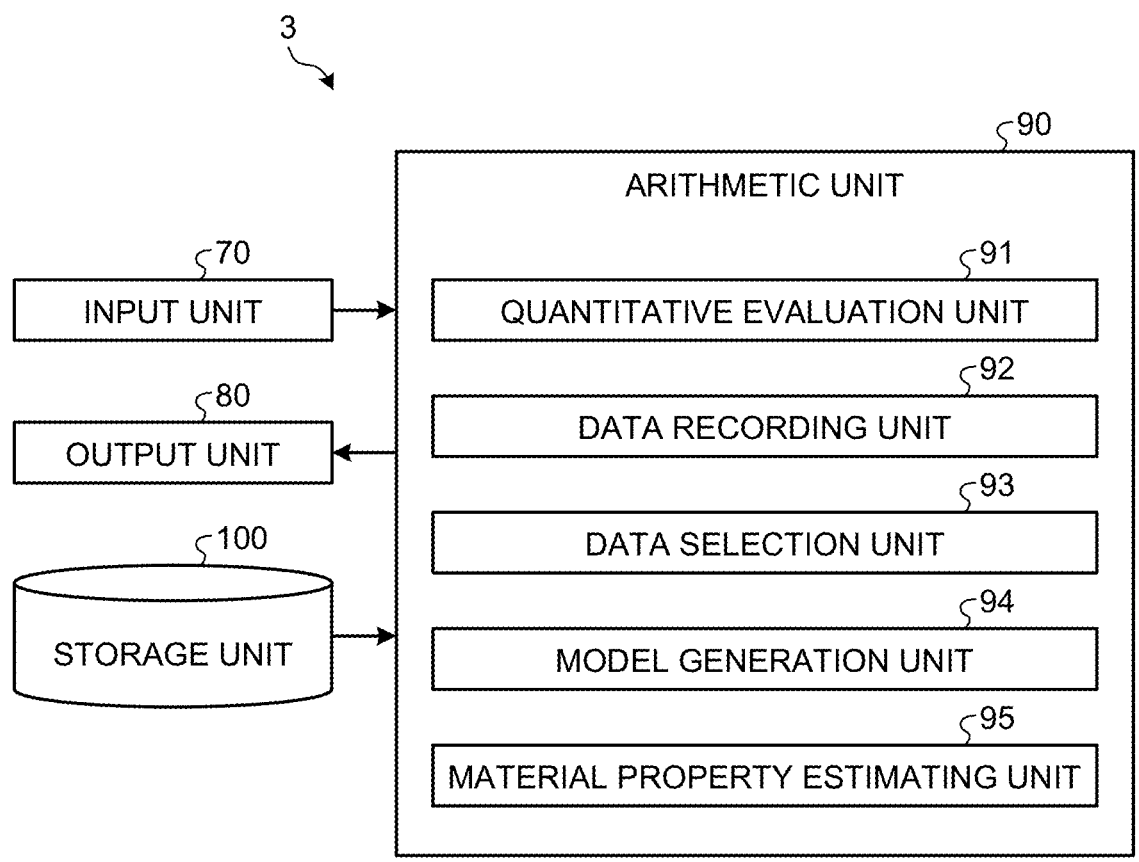
FIG. 6 is a block diagram illustrating a schematic configuration of a material property estimating device for a metal material according to an example.

In addition, the photographing condition determining device 1, the photographing device, the phase classification device, and the material property estimating device 3 have been described as one configuration as illustrated in FIGS. 1 and 6. However, the photographing condition determining device 1, the photographing device, the phase classification device, and the material property estimating device 3 may be implemented by separate devices or may be implemented by a single device.

In this example, the two-phase steel plate has been described as an example, however our concepts can also be applied to a steel plate of three or more phases.

The invention claimed is:

1. A photographing condition determining method for photographing a metal structure of a metal material, the photographing condition determining method comprising:
   a photographing step of photographing a part of the metal structure of the metal material having been subjected to predetermined sample preparation under a predetermined photographing condition;
   a phase specification step of assigning, to pixels corresponding to one or a plurality of predetermined phases of the metal structure, labels of respective phases for an image photographed in the photographing step;
   a feature value calculating step of calculating one or more feature values for a pixel to which a label of one of the phases has been assigned in the phase specification step;
   a phase classification step of classifying the phases of the metal structure of the image by inputting a feature value calculated in the feature value calculating step to a model, which has been learned in advance using feature values assigned with labels of respective phases as input and labels of the respective phases as output, and acquiring a label of a phase of a pixel corresponding to the feature value that has been input; and
   a photographing condition determining step of determining a photographing condition when other parts of the metal structure are photographed based on a classification result of the phase classification step.

2. The method according to claim 1,
   wherein, in the photographing step, a part of the metal structure is photographed under a plurality of predetermined photographing conditions, and
   in the photographing condition determining step, a photographing condition with which a classification accuracy of the phases in the phase classification step is the highest among the plurality of photographing conditions used in the photographing step is determined as a photographing condition for photographing the other parts of the metal structure.

3. The method according to claim 1, wherein the photographing condition includes at least one of a contrast value, a brightness value, and an intensity of a light source.

4. The method according to claim 1, further comprising, before the photographing step:
   a polishing step of roughly polishing the metal material and then performing buffing using a polishing material of 0.05 μm to 2 μm; and
   an etching step of etching the metal material using a nital solution prepared by mixing ethanol and nitric acid and has a nitric acid concentration of 0.5% to 8%.

5. A photographing method for a metal structure, wherein the other parts of the metal structure of the metal material are photographed under the photographing condition determined by the photographing condition determining method after the photographing condition determining method for a metal structure according to claim 1.

6. A phase classification method for a metal structure, comprising the steps of: photographing the metal structure by the photographing method for a metal structure according to claim 5; and classifying phases of the metal structure.

7. A material property estimating method for a metal material for estimating a material property of the metal material, the material property estimating method comprising, after the method according to claim 6:
   a quantitative evaluation step of calculating a quantitative evaluation value of the metal structure by calculating a size, an area ratio, or a shape of each of the classified phases;
   a data selection step of selecting data to be used for estimation of a material property of the metal material from the quantitative evaluation value and material properties of the metal material prepared in advance;
   a model generating step of generating an estimation model for estimating a material property of the metal material using the data that has been selected; and
   a material property estimating step of estimating a material property of the metal material using the estimation model that has been generated.

8. A photographing condition determining method for photographing a metal structure of a metal material, the photographing condition determining method comprising:
   a photographing step of consecutively photographing a part of the metal structure having been subjected to predetermined sample preparation while a photographing condition is varied;
   a feature value calculating step of calculating one or more feature values for images photographed in the photographing step;
   a phase classification step of classifying phases of the metal structure of the image by inputting a feature value calculated in the feature value calculating step to a model, which has been learned in advance using feature values of pixels assigned with labels of one or a plurality of predetermined phases of the metal structure as input and labels of the respective phases as output, and acquiring a label of a phase of a pixel corresponding to the feature value that has been input; and
   a photographing condition determining step of determining a photographing condition when other parts of the metal structure are photographed from among a plurality of photographing conditions used in the photographing step based on a classification result of the phase classification step.

9. The method according to claim 8, wherein, in the photographing condition determining step, a photographing condition under which a classification accuracy of the phases in the phase classification step is a highest among the photographing conditions used in the photographing step is determined as a photographing condition for photographing the other parts of the metal structure.

10. The method according to claim 8, wherein the photographing condition includes at least one of a contrast value, a brightness value, and an intensity of a light source.

11. The method according to claim 8, further comprising, before the photographing step:
   a polishing step of roughly polishing the metal material and then performing buffing using a polishing material of 0.05 μm to 2 μm; and
   an etching step of etching the metal material using a nital solution which is prepared by mixing ethanol and nitric acid and has a nitric acid concentration of 0.5% to 8%.

12. A photographing method for a metal structure, wherein the other parts of the metal structure of the metal material are photographed under the photographing condition determined by the photographing condition determining method after the method according to claim 8.

13. A phase classification method for a metal structure, comprising the steps of: photographing the metal structure by the method according to claim 12; and classifying phases of the metal structure.

14. A photographing condition determining device for photographing a metal structure of a metal material, the photographing condition determining device comprising:
   a photographing unit that photographs a part of the metal structure of the metal material having been subjected to predetermined sample preparation under a predetermined photographing condition;
   a phase specification unit that assigns, to pixels corresponding to one or a plurality of predetermined phases of the metal structure, labels of respective phases for an image photographed by the photographing unit;
   a feature value calculating unit that calculates one or more feature values for a pixel to which a label of one of the phases has been assigned by the phase specification unit;
   a phase classification unit that classifies the phases of the metal structure of the image by inputting a feature value calculated by the feature value calculating unit to a model, which has been learned in advance using feature values assigned with labels of respective phases as input and labels of the respective phases as output, and acquiring a label of a phase of a pixel corresponding to the feature value that has been input; and
   a photographing condition determining unit that determines a photographing condition when other parts of the metal structure are photographed based on a classification result of the phase classification unit.

15. A photographing device for a metal structure, wherein the other parts of the metal structure of the metal material are photographed under the photographing condition determined by the photographing condition determining device according to claim 14.

16. A phase classification device for a metal structure, wherein the metal structure is photographed by the photographing device for a metal structure according to claim 15, and phases of the metal structure are classified.

17. A photographing condition determining device for photographing a metal structure of a metal material, the photographing condition determining device comprising:
   a photographing unit that consecutively photographs a part of the metal structure having been subjected to predetermined sample preparation while a photographing condition is varied;
   a feature value calculating unit that calculates one or more feature values for images photographed by the photographing unit;
   a phase classification unit that classifies phases of the metal structure of the image by inputting a feature value calculated in the feature value calculating unit to a model, which has been learned in advance using feature values of pixels assigned with labels of one or a plurality of predetermined phases of the metal structure as input and labels of the respective phases as output, and acquiring a label of a phase of a pixel corresponding to the feature value that has been input; and
   a photographing condition determining unit that determines a photographing condition when the other parts of the metal structure are photographed from among a plurality of photographing conditions used in the photographing unit based on a classification result of the phase classification unit.

18. A photographing device for a metal structure, wherein the other parts of the metal structure of the metal material are photographed under the photographing condition determined by the device according to claim 17.

19. A phase classification device for a metal structure, wherein the metal structure is photographed by the device according to claim 18, and phases of the metal structure are classified.

20. A material property estimating device for a metal material for estimating a material property of the metal material, the material property estimating device comprising:
   an input unit that inputs an image in which phases of a metal structure have been classified;
   a quantitative evaluation unit that calculates a quantitative evaluation value of the metal structure by calculating a size, an area ratio, or a shape of each of the classified phases;
   a data recording unit that records the quantitative evaluation value in a database;
   a data selection unit that selects data to be used for estimation of a material property of the metal material from among the quantitative evaluation value and material properties of the metal material recorded in the database;
   a model generation unit that generates an estimation model for estimating a material property of the metal material using the data that has been selected;
   a material property estimating unit that estimates a material property of the metal material using the estimation model that has been generated; and
   an output unit that outputs the material property of the metal material that has been estimated.

\* \* \* \* \*